(12) United States Patent
Klinman et al.

(10) Patent No.: US 8,232,259 B2
(45) Date of Patent: Jul. 31, 2012

(54) MULTIPLE CPG OLIGODEOXYNUCLEOTIDE AND THEIR USE TO INDUCE AN IMMUNE RESPONSE

(75) Inventors: Dennis Klinman, Potomac, MD (US); Ken Ishii, Columbia, MD (US); Daniela Verthelyi, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/026,032

(22) Filed: Feb. 11, 2011

(65) Prior Publication Data

US 2011/0189267 A1 Aug. 4, 2011

Related U.S. Application Data

(60) Continuation of application No. 11/801,984, filed on May 10, 2007, now Pat. No. 7,919,477, which is a division of application No. 10/194,035, filed on Jul. 12, 2002, now Pat. No. 7,521,063, which is a continuation-in-part of application No. PCT/US01/01122, filed on Jan. 12, 2001.

(60) Provisional application No. 60/176,115, filed on Jan. 14, 2000.

(51) Int. Cl.
- A61K 39/00 (2006.01)
- A61K 39/38 (2006.01)
- A61K 45/00 (2006.01)
- A61K 47/00 (2006.01)
- A61K 31/70 (2006.01)
- A61K 9/127 (2006.01)

(52) U.S. Cl. ............... 514/44 R; 424/184.1; 424/278.1; 424/450

(58) Field of Classification Search .................. None
See application file for complete search history.

(56) References Cited

U.S. PATENT DOCUMENTS

| | | | |
|---|---|---|---|
| 4,469,863 A | 9/1984 | Ts'o et al. | |
| 5,023,243 A | 6/1991 | Tullis | |
| 5,663,153 A | 9/1997 | Hutcherson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,423,539 B2 | 7/2002 | Fong et al. | |
| 6,428,788 B1 | 8/2002 | Debinski et al. | |
| 6,429,199 B1 | 8/2002 | Krieg et al. | |
| 6,498,148 B1 | 12/2002 | Raz | |
| 6,514,948 B1 | 2/2003 | Raz et al. | |
| 6,534,062 B2 | 3/2003 | Raz et al. | |
| 6,552,006 B2 | 4/2003 | Raz et al. | |
| 6,562,798 B1 | 5/2003 | Schwartz | |
| 6,589,940 B1 | 7/2003 | Raz et al. | |
| 6,610,661 B1 | 8/2003 | Carson et al. | |
| 6,613,751 B2 | 9/2003 | Raz et al. | |
| 6,653,292 B1 | 11/2003 | Krieg et al. | |
| 6,949,520 B1 | 9/2005 | Hartmann et al. | |
| 6,977,245 B2 | 12/2005 | Klinman et al. | |
| 7,354,909 B2* | 4/2008 | Klinman et al. | 514/44 R |
| 7,521,063 B2* | 4/2009 | Klinman et al. | 424/282.1 |
| 7,615,227 B2 | 11/2009 | Klinman et al. | |
| 7,666,674 B2 | 2/2010 | Klinman et al. | |
| 7,758,876 B2 | 7/2010 | Klinman et al. | |
| 7,776,344 B2 | 8/2010 | Hartmann et al. | |
| 7,879,810 B2* | 2/2011 | Krieg et al. | 514/44 A |
| 7,892,569 B2* | 2/2011 | Klinman et al. | 424/278.1 |
| 7,919,477 B2* | 4/2011 | Klinman et al. | 514/44 R |
| 7,935,351 B2* | 5/2011 | Klinman et al. | 424/198.1 |
| 7,959,934 B2* | 6/2011 | Klinman et al. | 424/278.1 |
| 7,960,356 B2 | 6/2011 | Klinman et al. | |
| 8,008,266 B2* | 8/2011 | Krieg et al. | 514/44 R |
| 8,030,285 B2* | 10/2011 | Klinman et al. | 514/44 R |
| 8,043,622 B2* | 10/2011 | Klinman et al. | 424/184.1 |
| 8,053,422 B2* | 11/2011 | Klinman et al. | 514/44 R |
| 8,058,249 B2* | 11/2011 | Krieg et al. | 514/44 R |
| 8,114,848 B2* | 2/2012 | Krieg et al. | 514/44 R |
| 8,129,351 B2* | 3/2012 | Krieg et al. | 514/44 A |
| 8,148,340 B2* | 4/2012 | Krieg et al. | 514/44 R |
| 2001/0034330 A1 | 10/2001 | Kensil | |
| 2001/0036462 A1 | 11/2001 | Fong et al. | |
| 2001/0044416 A1 | 11/2001 | McCluskie et al. | |
| 2001/0046967 A1 | 11/2001 | Van Nest | |
| 2002/0006403 A1 | 1/2002 | Yu et al. | |
| 2002/0028784 A1 | 3/2002 | Nest | |

(Continued)

FOREIGN PATENT DOCUMENTS

EP 0 468 520 A2 1/1991

(Continued)

OTHER PUBLICATIONS

Coban et al, J. Leukoc. Biol. 78:647-655; 2005.* Gursel et al, J. Leukoc. Biol. 71: 813-820; 2002.*
Lee et al, Yonsei Medical Journal, 2005, 46/3:341-346.*
Verthelyi et al, Clinical Immunology 109 (2003) 64-71.*
Kreig (BioDrugs 1998, 5:341-346).*
Agarwal et al. (Trends in Mol. Med., 2002; 8:114-121).*
Hartmann et al. (J. Immunology, 2000; 164:1617-1624).*
Weiner (J. Leukocyte Biology, 68:456-463, 2000).*
Agarwal et al, Molecular Med, Today, 6:72-81, 2000.*
Zhao et al (Biochemical Pharmacology, 51:173-182, 1996.*
Alama et al., "Antisense Oligonucleotides as Therapeutic Agents," *Pharmacol. Res.* 36: 171-178 (1997).
Anfossi et al., "An oligomer complementary to c-myb-encoded mRNA inhibits proliferation of human myeloid leukemia cell lines" *Proc. Natl. Acad. Sci. USA* 86:3379-3383 (1989).
Ballas et al., "Induction of NK Activity in Murine and Human Cells by CpG Motifs in Oligodeoxynucleotides and Bacterial DNA," *J. Immun.* 157: 1840-1845 (1996).

(Continued)

Primary Examiner — Nita M Minnifield
(74) Attorney, Agent, or Firm — Klarquist Sparkman LLP

(57) ABSTRACT

Compositions including multiple oligodeoxynucleotides with a CpG motif are disclosed herein. The compositions can include either D or K type oligodeoxynucleotides. These compositions are of use in inducing an immune response in a large percentage of the individuals in a population.

19 Claims, No Drawings

U.S. PATENT DOCUMENTS

| | | | |
|---|---|---|---|
| 2002/0042383 | A1 | 4/2002 | Yew et al. |
| 2002/0042387 | A1 | 4/2002 | Raz et al. |
| 2002/0055477 | A1 | 5/2002 | Van Nest et al. |
| 2002/0064515 | A1 | 5/2002 | Krieg et al. |
| 2002/0065236 | A1 | 5/2002 | Yew et al. |
| 2002/0086295 | A1 | 7/2002 | Raz et al. |
| 2002/0086839 | A1 | 7/2002 | Raz et al. |
| 2002/0090724 | A1 | 7/2002 | Taylor et al. |
| 2002/0091095 | A1 | 7/2002 | Phillips et al. |
| 2002/0091097 | A1 | 7/2002 | Bratzler et al. |
| 2004/0052763 | A1 | 3/2004 | Mond et al. |
| 2007/0202575 | A1 | 8/2007 | Klinman et al. |
| 2009/0263405 | A1 | 10/2009 | Verthelyi et al. |
| 2010/0113565 | A1 | 5/2010 | Gorden et al. |
| 2010/0226941 | A1 | 9/2010 | Klinman et al. |
| 2011/0033421 | A1* | 2/2011 | Hartmann et al. ........... 424/85.7 |
| 2011/0110883 | A1* | 5/2011 | Klinman et al. ............. 424/85.1 |
| 2011/0189267 | A1* | 8/2011 | Klinman et al. .............. 424/450 |
| 2011/0212135 | A1* | 9/2011 | Klinman et al. ........... 424/269.1 |

FOREIGN PATENT DOCUMENTS

| | | |
|---|---|---|
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 92/18522 | 10/1992 |
| WO | WO 93/17115 | 9/1993 |
| WO | WO 94/19945 | 9/1994 |
| WO | WO 95/18231 | 7/1995 |
| WO | WO 95/26204 | 10/1995 |
| WO | WO 96/02555 | 2/1996 |
| WO | WO 97/28259 | 8/1997 |
| WO | WO 98/11211 | 3/1998 |
| WO | WO 98/18810 | 5/1998 |
| WO | WO 98/37919 | 9/1998 |
| WO | WO 98/40100 | 9/1998 |
| WO | WO 98/49288 | 11/1998 |
| WO | WO 98/52581 | 11/1998 |
| WO | WO 98/55495 | 12/1998 |
| WO | WO 99/11275 | 3/1999 |
| WO | WO 99/51259 | 10/1999 |
| WO | WO 99/56755 | 11/1999 |
| WO | WO 99/58118 | 11/1999 |
| WO | WO 99/61056 | 12/1999 |
| WO | WO 99/62923 | 12/1999 |
| WO | WO 00/06588 | 2/2000 |
| WO | WO 00/20039 | 4/2000 |
| WO | WO 00/21556 | 4/2000 |
| WO | WO 00/61151 | 10/2000 |
| WO | WO 00/62787 | 10/2000 |
| WO | WO 00/67023 | 11/2000 |
| WO | WO 01/00232 | 1/2001 |
| WO | WO 01/02007 | 1/2001 |
| WO | WO 01/12223 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |

OTHER PUBLICATIONS

Bauer et al., "Bacterial CpG-DNA Triggers Activation and Maturation of Human CD11c−, CD123+ Dendritic Cells," *J. Immunol.* 166:5000-5007 (2001).

Benimetskaya et al., "Formation of a G-tetrad and higher order structures correlates with biological activity of the RelA (NF-kBp65) 'antisense' oligodeoxynucleotide," *Nucleic Acids Research* 25(13):2648-2656 (1997).

Boggs et al., "Characterization and modulation of immune stimulation by modified oligonucleotides," *Antisense Nucl. Acid Drug Dev.* 7(5):461-471 (1997).

Branda et al., "Amplification of antibody production by phosphorothioate oligodeoxynucleotides," *J. Lab Clin. Med.* 128(3):329-338 (1996).

Chu et al., "CpG oligodeoxynucleotides act as adjuvants that switch on T helper 1 (Th1) immunity," *J. Exp. Med.* 186(10):1623-1631 (1997).

Decision of Interference No. 105,171, *The Regents of California* versus *University of Iowa, Coley Pharmaceutical Group, Inc. and The United States of America* (Jul. 17, 2006).

Deml et al., "Immunostimulatory CpG motifs trigger a T Helper-1 immune response to Human Immunodeficiency Virus Type-1 (HIV-1) gp160 envelope protein," *Clin. Chem. Lab. Med.* 37(3):199-204 (1999).

Gao et al., "Phosphorothioate oligonucleotides are inhibitors of human DNA polymerases and Rnase H: Implications for antisense technology," *Mol. Pharmacol.* 41:223-229 (1992).

Gursel et al., "Differential and Competitive Activation of Human Immune Cells by Distinct Classes of CpG Oligodeoxynucleotide," *J. Leuko. Biol.* 71:813-820 (2002).

Halpern et al., "Bacterial DNA induces murine interferon-gamma production by stimulation of interleukin-12 and tumor necrosis factor-alpha," *Cell Immunol.* 167(1):72-78 (1996).

Ishibashi et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities," *Cancer Research* 60:6531-6536 (2000).

Iversen et al., "Pharmacokinetics of an antisense phosphorothioate oigodeoxynucleotide against rev from human immunodeficiency virus type 1 in the adult male rat following single inections and continuous infusion," *Antisense Res. Dev.* 4:43-52 (1994).

Jilek et al., "Antigen-Independent Suppression of the Allergic Immune Response to Bee Venom Phospholipase A2 by DNA Vaccination in CBA/J Mice," *J. Immunol.* 166:3612-3621 (2001).

Kadowaki et al., "Distinct CpG DNA and Poly inosinic-Polycytidylic Acid Double Stranded RNA, Respectively, Stimulate CD11c− Type 2 Dendritic Cell Precursoes and CD11c+ Dendritic cells to Produce Type I IFN," *J. Immunol.* 166:2291-2295 (2001).

Klinman et al., "Activation of the innate immune system by CpG oligodeoxynucleotides: immunoprotective activity and safety," *Springer Semin. Immunopathol.* 22:173-183 (2000).

Klinman et al., "CpG Motifs as Immune Adjuvants," *Vaccine* 17: 19-25 (1999).

Klinman et al., "CpG Motifs Present in Bacterial DNA Rapidly Induce Lymphocytes to Secrete Interleukin 6, Interleukin 12 and Interferon γ," *Proc. Natl. Acad. Sci. USA* 93: 2879-2883 (1996).

Krieg et al., "A role for endogenous retroviral sequences in the regulation of lymphocyte activation," *J. Immunol.* 143(8):2448-2451 (1989).

Krieg et al., "Brief Communication: Oligodeoxynucleotide Modifications Determine the Magnitude of B-Cell Stimulation by CpG Motifs," *Antisense & Nucleic Acid Drug Development* 6:133-139 (1996).

Krieg et al., "CpG DNA: A pathogenic factor in systemic lupus erythematosus?," *J. Clin. Immunol.* 15(6):284-292 (1995).

Krieg et al., "CpG motifs in bacterial DNA and their immune effect," *Annu. Rev. Immunol.* 20:709-760 (2002).

Krieg et al., "CpG motifs in bacterial DNA trigger direct B-cell activation," *Nature* 374:546-549 (1995).

Krieg et al., "Leukocyte stimulation by oligodeoxynucleotides," *Applied Antisense Oligonucleotide Tech.* (BOOK):431-448 (1998).

Krug et al., "Identification of CpG Oligonucleotide Sequences with High Induction of IFN-α/β in Plasmacytoid Dendritic Cells," *Eur. J. Immunol.* 31:2154-2163 (2001).

Krug et al., "Toll-like Receptor Expression Reveals CpG DNA as a Unigue Microbial Stimulus for Plasmacytoid Dendritic Cells Which Synergizes With CD40 Ligand to Induce High Amounts of IL-12," *Eur. J. Immunol.* 31:3026-3037 (2001).

Kuramoto et al., "Oligonucleotide sequences required for natural killer cell activation," *Jpn. J. Cancer Res.* 83:1128-1131 (1992).

Lang et al., "Guanosine-rich oligodeoxynucleotides induce proliferation of macrophage progenitors in cultures of murine bone marrow cells," *Eur. J. Immunol.* 29:3496-3506 (1999).

Lapatschek, et al., "Activation of Macrophages and B Lymphocytes by an Oligodeoxynucleotide Derived from an Acutely Pathogenic Simian Immunodeficiency Virus," *Antisense Nucleic Acid Drug Dev.* 8(5):357-370 (1998).

Liang et al., "Activation of Human B Cells by Phosphorothioate Oligodeoxynucleotides," *J. Clin. Invest.* 98: 1119-1129 (1996).

Lonnberg et al., "Towards Genomic Drug Therapy with Antisense Oligonucleotides," *Ann. Med.* 28: 511-522 (1996).

Maltese et al., "Sequence context of antisense RelA/NF-kB phohphorothioates determines specificity," *Nucleic Acids Research* 23(7):1146-1151 (1995).

Manzel et al., "Lack of Immune Stimulation by Immobilized CpG-oligonucletide," *Antisense & Nucleic Acid Drug Development* 9(5):459-464 (1999).

Matson et al., "Nonspecific suppression of [3H]thymidine incorporation by control oligonucleotides," *Antisense Res. Dev.* 2(4):325-330 (1992).

McCluskie et al., "CpG DNA is a Potent Enhancer of Systemic & Mucosal Immune Response Against Hepatitis B Surface Antigen with Intra-Nasal Administration to Mice," *J. Immun.* 161: 4463-4465 (1998).

McIntyre et al., "A sense phosphorothioate oligonucleotide directed to the initiation codon of transcription factor NF-kappa B p65 causes sequence-specific immune stimulation," *Antisense Res. Dev.* 3(4):309-322 (1993).

Mutwiri et al., "Biological activity of immunostimulatory CpG DNA motifs in domestic animals," *Veterinary Immunology and Immunopathology* 91:89-103 (2003).

Oberbauer, "Not Non-Sense but Antisense-Applications of Antisense Oligonucleotides in Different Fields of Medicine," *Wein Klin Wochenschr* 109: 40-46 (1997).

Pisetsky, "Immunological consequences of nucleic acid therapy," *Antisense Res. Dev.* 5:219-225 (1995).

Prasad et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide," *Antimicrobial Agents and Chemotherapy* 43(11):2689-2696 (Nov. 1999).

Raz et al., "Intradermal gene immunization: the possible role of DNA uptake in the induction of cellular immunity to viruses," *Proc. Natl. Acad. Sci. USA* 91:9519-9523 (1994).

Roman et al., "Immunostimulatory DNA sequences function as T helper-1-promoting adjuvants," *Nature Med.* 3(8):849-854 (1997).

Scanlon et al., "Oligonucleotide-Mediated Modulation of Mammalian Gene Expression," *FASEB J.* 9: 1288-1295 (1995).

Schwartz et al., "CpG motifs in bacterial DNA cause inflammation in the lower respiratory tract," *J. Clin. Invest.* 100(1):68-73 (1997).

Stacey et al., "Immunostimulatory DNA as an adjuvant in vaccination against Leishmania major," *Infect. Immun.* 67:3719-3726 (1999).

Tokunaga et al., "A synthetic single-stranded DNA, poly(dG, dC), induces interferon-$\alpha/\beta$ and -$\gamma$, augments natural killer activity and suppresses tumor growth," *Jpn. J. Cancer Res.* 79:682-686 (1988).

Tokunaga et al., "Synthetic oligonucleotides with particular base sequences from the cDNA encoding proteins of Mycobacterium bovis BCG induce interferons and activate natural killer cells," *Microbiol. Immunol.* 36(1):55-66 (1992).

Verthelyi et al., "CpG Oligodeoxynucleotides as Vaccine Adjuvants in Primates," *J. Immunol.* 168:1659-1663 (2002).

Verthelyi et al., "Human Peripheral Blood Cells Differentially Recognize and Respond to Two Distinct CpG Motifs," *J. Immunol.* 166:2372-2377 (2001).

Weiner et al., "Immunostimulatory oligodeoxynucleotides containing the CpG motif are effective as immune adjuvants in tumor antigen immunization," *Proc. Natl. Acad. Sci. USA* 94:10833-10837 (1997).

Yamamoto et al., "Ability of oligonucleotides with certain palindromes to induce interferon production and augment natural killer cell activity is associated with their base length," *Antisense Res. Dev.* 4:119-123 (1994).

Yamamoto et al., "Lipofection of synthetic oligodeoxyribonucleotide having a palindromic sequence AACGTT to murine splenocytes enhances interferon production and natural killer activity," *Microbiol. Immunol.* 38(10):831-836 (1994).

Yamamoto et al., "Synthetic oligonucleotides with certain palindromes stimulate interferon production of human peripheral blood lymphocytes in vitro," *Jpn. J. Cancer Res.* 85:775-779 (1994).

Yamamoto, "Unique palindromic sequences in synthetic oligonucleotides are required to induce inf and augment INF-mediated natural killer activity," *J. Immunol.* 148(12):4072-4076 (1992).

Yamamoto, et al., "Mode of action of oligonucleotide fraction extracted from Mycobacterium bovis BeG," *Kekkaku* 69(9):29-32 (1994).

Yaswen et al., "Effects of Sequence of Thioated Oligonucleotides on Cultured Human Mammary Epithelial Cells," *Antisense Research and Development* 3:67-77 (1993).

Yi et al., "IFN-$\gamma$ promotes IL-6 and IgM secretion in response to CpG motifs in bacterial DNA and oligonucleotides," *J. Immunol.* 156:558-564 (1996).

Yi et al., "Rapid Immune Activation by CpG Motifs in Bacterial DNA," *J. Immun.* 157: 5394-5402 (1996).

Zelphati et al., "Inhibition of HIV-1 Replication in Cultured Cells with Antisense Oligonucleotides Encapsulated in Immunoliposomes," *Antisense Res. Dev.* 3:323 (1993).

\* cited by examiner

MULTIPLE CPG OLIGODEOXYNUCLEOTIDE AND THEIR USE TO INDUCE AN IMMUNE RESPONSE

PRIORITY CLAIM

This is a continuation of U.S. patent application Ser. No. 11/801,984, filed May 10, 2007, issued as U.S. Pat. No. 7,919,477, which is a divisional application of U.S. patent application Ser. No. 10/194,035, filed on Jul. 12, 2002, issued as U.S. Pat. No. 7,521,063, which is a continuation-in-part of PCT Application No. PCT/US01/01122 filed on Jan. 12, 2001, which claims the benefit of U.S. Provisional Patent Application No. 60/176,115 filed on Jan. 14, 2000. The prior applications are incorporated herein by reference in their entirety.

FIELD

This application relates to oligodeoxynucleotides including a CpG motif, specifically to the use of multiple oligodeoxynucleotides including a CpG motif for inducing an immune response.

BACKGROUND

DNA is a complex macromolecule whose immunological activities are influenced by its base composition and base modification, as well as helical orientation. Certain unusual DNA structures (e.g., Z-DNA) can induce significant antibody responses when administered to normal mice. In addition, bacterial DNA, as well as certain synthetic unmethylated CpG sequences can induce proliferation and immunoglobulin (Ig) production by murine B cells. Unmethylated CpG dinucleotides are more frequent in the genomes of bacteria and viruses than vertebrates. Recent studies suggest that immune recognition of these motifs may contribute to the host's innate immune response. D. M. Klinman et al., "CpG Motifs Present in Bacterial DNA Rapidly Induce Lymphocytes to Secrete Interleukin 6, Interleukin 12, and Interferon γ," 93 *Proc. Natl. Acad. Sci. USA* 2879 (1996); A.-K. Yi et al., "Rapid Immune Activation by CpG Motifs in Bacterial DNA," 157 *J. Immun.* 5394 (1996); Hua Liang et al., "Activation of Human B Cells by Phosphorothioate Oligodeoxynucleotides," 98 *J. Clin. Invest.* 1119 (1996); A. M. Krieg et al., "CpG Motifs in Bacterial DNA Trigger Direct B-Cell Activation," 374 *Nature* 546 (1995).

In mice, CpG DNA induces proliferation in almost all (>95%) of B cells and increases Ig secretion. This B cell activation by CpG DNA is T cell independent and antigen non-specific. In addition to its direct effects on B cells, CpG DNA also directly activates monocytes, macrophages, and dendritic cells to secrete a variety of cytokines. These cytokines stimulate natural killer (NK) cells to secrete γ-inteferon (IFN-γ) and have increased lytic activity. Examples of which can be found in International Patent Applications WO 95/26204, WO 96/02555, WO 98/11211, WO 98/18810, WO 98/37919, WO 98/40100, WO 98/52581, and PCT/US98/047703; U.S. patent applications Ser. Nos. 08/738,652 and 09/136,138; and U.S. Pat. No. 5,663,153.

Although bacterial DNA and certain CpG sequences can induce responses from human cells (Ballas et al., "Induction of NK Activity in Murine and Human Cells by CpG Motifs in Oligodeoxynucleotides and Bacterial DNA," 157 *J. Immunol.* 1840 (1996)), individual subjects show considerable heterogeneity in their response to different CpG sequences. As disclosed herein, CpG sequences that strongly stimulate cells from some subjects are virtually inactive on cells from other subjects. These different responses can make it difficult to induce a therapeutic immune response in all members of a diverse population using a single CpG sequence, even if such a sequence is expressed repetitively in a given oligodeoxynucleotide. Thus, there exists a need to identify different CpG sequences that together are capable of optimally inducing an immune response in cells from all members of a target population.

SUMMARY

Compositions including multiple oligodeoxynucleotides with a CpG motif are disclosed herein. These compositions are of use in inducing an immune response in a large percentage of the individuals in a population.

In one embodiment, an oligodeoxynucleotide composition is disclosed that includes at least two oligodeoxynucleotides of at least about 10 nucleotides in length, wherein the oligodeoxynucleotides each include an unmethylated CpG motif. In this composition, the oligodeoxynucleotides have a sequence represented by the formula 5' $N_1N_2N_3$Q-CpG-W$N_4N_5N_6$ 3', wherein Q is T or G or A, W is A or T, and $N_1$, $N_2$, $N_3$, $N_4$, $N_5$, and $N_6$ are any nucleotide. The two oligodeoxynucleotides differ in their nucleic acid sequence. In one embodiment, the oligodeoxynucleotide compositions are used to induce an immune response. In one specific, non-limiting example, the oligodeoxynucleotide compositions are used to induce an immune response in at least about 80% of a population. In one specific, non-limiting example, a single parameter of the immune response can be increased. In another specific, non-limiting example, administration of the at least two oligodeoxynucleotides broadens the immune response. For example, more parameters of the immune response are increased by administering the at least two oligodeoxynucleotides including a CpG motif, than are stimulated upon administration of only one of the oligodeoxynuleotides including a CpG motif.

In another embodiment, an oligodeoxynucleotide composition is disclosed that includes at least two oligodeoxynucleotides of at least about 10 nucleotides in length, wherein the oligodeoxynucleotides comprise an unmethylated CpG motif, wherein the oligodeoxynucleotides include a sequence represented by the formula 5' RY-CpG-RY 3', wherein R is A or G and Y is C or T. The at least two oligodeoxynucleotides differ in their nucleic acid sequence. In one embodiment, the oligodeoxynucleotide compositions are used to induce an immune response. In one specific, non-limiting example, the oligodeoxynucleotide compositions are used to induce an immune response in at least about 80% of a population. In one specific, non-limiting example, a single parameter of the immune response can be increased. In another specific, non-limiting example, administration of the at least two oligodeoxynucleotides broadens the immune response. Thus, more parameters of the immune response are increased by administering the at least two oligodeoxynucleotides that include a CpG motif, than are stimulated upon administration of only one of the oligodeoxynuleotides that includes a CpG motif.

The foregoing and other features and advantages will become more apparent from the following detailed description of several embodiments.

Sequence Listing

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file [4239-63317-03_Sequence_Listing.txt, Feb. 10, 2011, 23.7 KB], which is incorporated by reference herein.

DETAILED DESCRIPTION

I. Abbreviations

| | |
|---|---|
| A: | adenine |
| Ab: | antibody |
| APC: | antigen presenting cell |
| C: | cytosine |
| APC: | antigen presenting cell |
| CpG ODN: | an oligodeoxynucleotide (either a D or a K type) including a CpG motif. |
| DC: | dendritic cell |
| FCS: | fetal calf serum |
| G: | guanine |
| h: | hour |
| HKLV: | heat-killed leishmania vaccine |
| IFN-α: | interferon alpha |
| IFN-γ: | interferon gamma |
| IL-10: | interleukin 10 |
| IL-6: | interleukin 6 |
| mm: | millimeter |
| mRNA: | messenger ribonucleic acid. |
| ODN: | oligodeoxynucleotide |
| Pu: | purine |
| Py: | pyrimidine |
| s.c.: | subcutaneaous |
| T: | thymine |
| μg: | microgram |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Allergen: A substance that can induce an allergic or asthmatic response in a susceptible subject. The list of allergens is enormous and can include pollens, insect venoms, animal dander dust, fungal spores and drugs (e.g. penicillin). Examples of natural, animal and plant allergens include proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia*); *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides*, *Juniperus virginiana*, *Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*). The term "allergy" refers to acquired hypersensitivity to a substance (allergen). An "allergic reaction" is the response of an immune system to an allergen in a subject allergic to the allergen. Allergic conditions include eczema, allergic rhinitis or coryza, hay fever, bronchial asthma, urticaria (hives) and food allergies, and other atopic conditions.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Anti-infectious agent: A substance (such as a chemical compound, protein, antisense oligonucleotide, or other molecule) of use in treating infection of a subject. Anti-infectious agents include, but are not limited to, anti-fungals, anti-virals, and antibiotics.

Animal: Living multi-cellular vertebrate organisms, a category that includes, for example, mammals and birds. The term mammal includes both human and non-human mammals. Similarly, the term "subject" includes both human and veterinary subjects.

Asthma: A disorder of the respiratory system characterized by inflammation, narrowing of the airways and increased reactivity of the airways to inhaled agents. Asthma is frequently, although not exclusively associated with atopic or allergic symptoms.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligodeoxynucleotide is an oligodeoxynucleotide that is at least about ten nucleotides in length and includes an unmethylated CpG. CpG oligodeoxynucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cancer: A malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., ©2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Cytokine. Proteins made by cells that affect the behavior of other cells, such as lymphocytes. In one embodiment, a cytokine is a chemokine, a molecule that affects cellular trafficking. Specific non-limiting examples of cytokines are IFN-γ, IL-6, and IL-10.

D Type Oligodeoxynucleotide (D ODN): An oligodeoxynucleotide including an unmethylated CpG motif that has a sequence represented by the formula:

5' RY-CpG-RY 3' wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D type ODN is at least about 16 nucleotides in length and includes a sequence represented by Formula III:

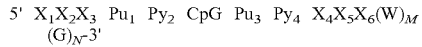

5' $X_1X_2X_3$ $Pu_1$ $Py_2$ CpG $Pu_3$ $Py_4$ $X_4X_5X_6(W)_M$ $(G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10. Additional detailed description of D ODN sequences and their activities can be found in the section entitled "Multiple D and K Type Oligodeoxynucleotides (ODN) that Include a CpG Motif." Generally D ODNs can stimulate a cellular response. For example, D ODNs stimulate natural killer cells and the maturation of dendritic cells.

Dendritic cell (DC): Dendritic cells are the principle antigen presenting cells (APCs) involved in primary immune responses. Their major function is to obtain antigen in tissues, migrate to lymphoid organs and present the antigen in order to activate T cells.

When an appropriate maturational cue is received, DC are signaled to undergo rapid morphological and physiological changes that facilitate the initiation and development of immune responses. Among these are the up-regulation of molecules involved in antigen presentation; production of pro-inflammatory cytokines, including IL-12, key to the generation of Th1 responses; and secretion of chemokines that help to drive differentiation, expansion, and migration of surrounding naive Th cells. Collectively, these up-regulated molecules facilitate the ability of DC to coordinate the activation and effector function of other surrounding lymphocytes that ultimately provide protection for the host. Although the process of DC maturation is commonly associated with events that lead to the generation of adaptive immunity, many stimuli derived from the innate branch of the immune system are also capable of activating DC to initiate this process. In this manner, DC provide a link between the two branches of the immune response, in which their initial activation during the innate response can influence both the nature and magnitude of the ensuing adaptive response. A dendritic cell precursor is a cell that matures into an antigen presenting dendritic cell. In one embodiment, a dendritic cell is a plasmacytoid dendritic cell.

Differentiation: The process by which cells become more specialized to perform biological functions, and differentiation is a property that is totally or partially lost by cells that have undergone malignant transformation. For example, dendritic cell precursors undergo maturation to become APCs.

Epitope: An antigenic determinant. These are particular chemical groups or peptide sequences on a molecule that are antigenic, i.e. that elicit a specific immune response. An antibody binds a particular antigenic epitope.

Functionally Equivalent: Sequence alterations, for example in a D type ODN, that yield the same results as described herein. Such sequence alterations can include, but are not limited to, deletions, base modifications, mutations, labeling, and insertions.

Immune response: A response of a cell of the immune system, such as a B cell, T cell to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFN-γ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. One, specific, non-limiting example of a statistical test used to assess a substantial increase is the use of a Z test to compare the percent of samples that respond to multiple ODNs including a CpG motif as compared to the percent of samples that respond using a single ODN including a CpG motif. A non-paramentric ANOVA can be used to compare differences in the magnitude of the response induced by multiple ODNs including a CpG motif as compared to the percent of samples that respond using a single ODN. In this example, p≦0.05 is significant, and indicates a substantial increase in the parameter of the immune response. One of skill in the art can readily identify other statistical assays of use.

Immune system deficiency: A disease or disorder in which the subject's immune system is not functioning in normal capacity or in which it would be useful to boost a subject's immune response. Immune system deficiencies include those diseases or disorders in which the immune system is not functioning at normal capacity, or in which it would be useful to boost the immune system response. In one specific, non-limiting example, a subject with an immune system deficiency has a tumor or cancer (e.g. tumors of the brain, lung (e.g. small cell and non-small cell), ovary, breast, prostate, colon, as well as other carcinomas and sarcomas).

Infectious agent: An agent that can infect a subject, including, but not limited to, viruses, bacteria, and fungi.

Examples of infectious virus include: *Retroviridae; Picornaviridae* (for example, polio viruses, hepatitis A virus; enteroviruses, human coxsackie viruses, rhinoviruses, echoviruses); *Calciviridae* (such as strains that cause gastroenteritis); *Togaviridae* (for example, equine encephalitis viruses, rubella viruses); *Flaviridae* (for example, dengue viruses, encephalitis viruses, yellow fever viruses); *Coronaviridae* (for example, coronaviruses); *Rhabdoviridae* (for example, vesicular stomatitis viruses, rabies viruses); *Filoviridae* (for example, ebola viruses); *Paramyxoviridae* (for example, parainfluenza viruses, mumps virus, measles virus, respiratory syncytial virus); *Orthomyxoviridae* (for example, influenza viruses); *Bungaviridae* (for example, Hantaan viruses, bunga viruses, phleboviruses and Nairo viruses); *Arena viridae* (hemorrhagic fever viruses); *Reoviridae* (e.g., reoviruses, orbiviurses and rotaviruses); *Birnaviridae; Hepadnaviridae* (Hepatitis B virus); *Parvoviridae* (parvoviruses); *Papovaviridae* (papilloma viruses, polyoma viruses); *Adenoviridae* (most adenoviruses); *Herpesviridae* (herpes simplex virus (HSV) 1 and HSV-2, varicella zoster virus, cytomegalovirus (CMV), herpes viruses); *Poxviridae* (variola viruses, vaccinia viruses, pox viruses); and *Iridoviridae* (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (such as *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae, pathogenic Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include, but are not limited to, *Cryptococcus neoformans, Histoplasma capsulatum, Coccidioides immitis, Blastomyces dermatitidis, Chlamydia trachomatis, Candida albicans*.

Other infectious organisms (such as protists) include: *Plasmodium falciparum* and *Toxoplasma gondii*.

Interferon alpha: At least 23 different variants of IFN-α are known. The individual proteins have molecular masses between 19-26 kDa and consist of proteins with lengths of 156-166 and 172 amino acids. All IFN-α subtypes possess a common conserved sequence region between amino acid positions 115-151 while the amino-terminal ends are variable. Many IFN-α subtypes differ in their sequences at only one or two positions. Naturally occurring variants also include proteins truncated by 10 amino acids at the carboxy-terminal end.

There are at least 23 different IFN-α genes. They have a length of 1-2 kb and are clustered on human chromosome 9p22. Based upon the structures two types of IFN-alpha genes, designated class I and II, are distinguished. They encode proteins of 156-166 and172 amino acids, respectively.

IFN-α is assayed by a cytopathic effect reduction test employing human and bovine cell lines. Minute amounts of IFN-α can be assayed also by detection of the Mx protein specifically induced by this interferon. A sandwich ELISA employing bi-specific monoclonal antibodies for rapid detection is also available.

Interferon gamma: IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELSA test that allows detection of individual cells producing IFN-γ. Minute amounts of IFN-γ can be detected indirectly by measuring IFN-induced proteins such as Mx protein. The induction of the synthesis of IP-10 has been used also to measure IFN-gamma concentrations. In addition, bioassays can be used to detect IFN-γ, such as an assay that employs induction of indoleamine 2,3-dioxygenase activity in 2D9 cells.

Interferon Inducible Protein 10: A cytokine that is 98 amino acids in length that has homology to platelet factor-4, and is a chemokine. The human IP-10 genes contains four exons and maps to chromosome 4q12-21.

Interleukin-6: IL-6 is a cytokine that is 185 amino acids in length. This polypeptide is glycosylated at positions 73 and 172, and is synthesized as a precursor protein of 212 amino acids. Monocytes express at least five different molecular forms of IL-6 with molecular masses of 21.5-28 kDa. They mainly differ by post-translational alterations such as glycosylation and phosphorylation. IL-6 isolated from various cell types shows some microheterogeneity in its N-terminus.

The human IL-6 gene has a length of approximately 5 kb and contains five exons. It maps to human chromosome 7p21-p14 between the markers D7S135 and D7S370. The murine gene maps to chromosome 5. Human IL6 is biologically active in monkeys, rats, and mice.

IL-6 has a myriad of activities and has been demonstrated to influence antigen-specific immune responses and inflammatory reactions. It is one of the major physiological mediators of an acute immune response.

Interleukin-10: IL-10 is a homodimeric protein with subunits having a length of 160 amino acids that is a cytokine. Human IL-10 shows 73 percent amino acid homology with murine IL-10. The human IL-10 gene contains four exons.

IL-10 inhibits the synthesis of a number of cytokines such as IL-2 and IFN-γ in Th1 subpopulations of T-cells but not of Th2. IL-10 can be detected with an ELISA assay. In addition, the murine mast cell line D36 can be used to bioassay human IL-10. The intracellular factor can be detected also by flow cytometry.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

5' $N_1N_2N_3Q$-CpG-W$N_4N_5N_6$ 3' wherein the central CpG motif is unmethylated, Q is T, G or A, W is A or T, and $N_1$, $N_2$, $N_3$, $N_4$, $N_5$, and $N_6$ are any nucleotides. In one embodiment, Q is a T. Additional detailed description of K ODN sequences and their activities can be found in the section entitled "Multiple D and K Type Oligodeoxynucleotides (ODN) that Include a CpG Motif." Generally K ODNs can stimulate a humoral response. For example, K ODNs stimulate the production of IgM.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphomnuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Maturation: The process in which an immature cell, such as dendritic cell, changes in form or function to become a functional mature cell, such as an APC.

Neoplasm: An abnormal cellular proliferation, which includes benign and malignant tumors, as well as other proliferative disorders.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxynucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phophonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligodeoxynucleotide," "immunostimulatory CpG containing oligodeoxynucleotide," "CpG ODN," refers to an oligodeoxynucleotide, which contains a cytosine, guanine dinucleotide sequence and (e.g. has a mitogenic effect or induces cytokine production) vertebrate immune cells. In one embodiment, an immunostimulatory CpG ODN stimulates a parameter of an immune response in a subject. The cytosine, guanine is unmethylated.

An "oligonucleotide delivery complex" is an oligonucleotide associated with (e.g. ionically or covalently bound to; or encapsulated within) a targeting agent (e.g. a molecule that results in a higher affinity binding to a target cell (e.g. B-cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an autoimmune disorder. An example of a person with a known predisposition is someone with a history of diabetes in the family, or who has been exposed to factors that predispose the subject to a condition, such as lupus or rheumatoid arthritis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, in a purified preparation, the protein or peptide represents at least 50% of the total peptide or protein content of the preparation. Similarly, in a purified preparation of oligodeoxynucleotides, the oligodeoxynucleotide represents at least 50% of the total nucleic acid content of the preparation.

Self-complementary nucleic acid sequence: A nucleic acid sequence that can form Watson-Crick base pairs. The four bases characteristic of deoxyribonucleic unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that could form hydrogen bonds with 3, 4, 5, 6 or more bases, respectively, of the same nucleic acid sequence.

Therapeutically effective dose: A dose sufficient to prevent advancement, or to cause regression of a disease, or which is capable of relieving symptoms caused by a disease, such as pain or swelling.

Vaccine: A preparation of attenuated microorganisms (including but not limited to bacteria and viruses), living microorganisms, antigen, or killed microorganisms, administered for the prevention, amelioration or treatment of infectious disease.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Multiple D and K Type Oligodeoxynucleotides (ODNs) That Include a CpG Motif

Compositions are disclosed herein that include multiple oligodeoxynucleotides with a CpG motif, wherein the sequences of the oligodeoxynucleotides are different. The multiple oligodeoxynucleotides are either K type CpG ODNs or D type ODNs. These compositions are of use in inducing an immune response in a subject. The compositions include at least two ODNs including a CpG motif. Thus, for example, the compositions can include two, three, four, or five ODNs including a CpG motif. Each of the oligodeoxynucleotides has a different sequence.

I. K Type ODNs

An oligodeoxynucleotide (ODN) composition is disclosed herein that includes at least two oligodeoxynucleotides of at least about 10 nucleotides in length, wherein the oligodeoxy- nucleotides comprise an unmethylated CpG motif. In one embodiment, at least one of the oligodeoxynucleotides includes multiple CpG motifs. In another embodiment, each of the oligodeoxynucleotide includes a single CpG motif. The sequence of each of the oligodeoxynucleotides differs from the sequence of the other oligodeoxynucleotides.

In one embodiment, the ODNs are K type ODNs. K ODNs which exhibit the greatest immunostimulatory activity share specific characteristics. These characteristics differ from those of the Formula II or D ODN (see below). In addition, K ODN have specific effects on the cells of the immune system, which differ from the effects of D ODN. For example, K ODN stimulate production of IgM.

The K ODNs are least about 10 nucleotides in length and include a sequence represented by either Formula I:

wherein the central CpG motif is unmethylated, Q is T, G or A, W is A or T, and $N_1$, $N_2$, $N_3$, $N_4$, $N_5$, and $N_6$ are any nucleotides.

These Formula I or K ODN can stimulate B cell proliferation and the secretion of IgM and IL-6, and processes involved in the body's humoral immunity, such as the production of antibodies against foreign antigens. In one embodiment, the K ODNs induce a humoral immune response.

In one embodiment, K type oligodeoxynucleotides include a sequence represented by the formula

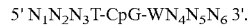

In another embodiment, K type oligodeoxynucleotides include a phosphate backbone modification. In one specific, non-limiting example, the phosphate backbone modification is a phosphorothioate backbone modification (i.e., one of the non-bridging oxygens is replaced with sulfur, as set forth in International Patent Application WO 95/26204, herein incorporated by reference). In one embodiment, K ODNs have a phophorothioate backbone, and at least one unmethylated CpG dinucleotide. Eliminating the CpG dinucleotide motif from the K ODN significantly reduces immune activation. Incorporating multiple CpGs in a single K ODN can increase immune stimulation. In one embodiment, the K ODN are at least 12 bases long. In addition, K ODN containing CpG motifs at the 5' end are the most stimulatory, although at least one base upstream of the CpG is required. More particularly, the most active K ODNs contain a thymidine immediately 5' from the CpG dinucleotide, and a TpT or a TpA in a position 3' from the CpG motif. Modifications which are greater than 2 base pairs from the CpG dinucleotide motif appear to have little effect on K ODN activity.

K-type CpG oligodeoxynucleotides can include modified nucleotides. Any suitable modification can be used to render the ODN resistant to in vivo degradation resulting from, e.g., exo or endonuclease digestion. In one embodiment, the modification includes a phosphorothioate modification. The phosphorothioate modifications can occur at either termini, e.g., the last two or three 5' and/or 3' nucleotides can be linked with phosphorothioate bonds. The ODN also can be modified to contain a secondary structure (e.g., stem loop structure) such that it is resistant to degradation. Another modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat.

No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

In one embodiment, a composition is provided that includes multiple different K type ODN (for example two, three, four or more different K type ODN). Thus, disclosed herein is an oligodeoxynucleotide composition including at least two different oligodeoxynucleotide of at least about 10 nucleotides in length, wherein the oligodeoxynucleotides include an unmethylated CpG motif that can be used to induce an immune response in a subject. Thus, the at least two ODNs in the composition include a sequence represented by the formula 5' $N_1N_2N_3$T-CpG-WN$_4$N$_5$N$_6$ 3', wherein W is A or T, and $N_1$, $N_2$, $N_3$, $N_4$, $N_5$, and $N_6$ are any nucleotide. In one embodiment, at least one of the oligodeoxynucleotides includes multiple CpG motifs. In another embodiment, the oligodeoxynucleotides each include only a single CpG motif. In these embodiments, the two or more oligodeoxynucleotides differ in their nucleic acid sequence.

One specific non-limiting example is a composition that includes an oligodeoxynucleotide including a sequence as set forth as SEQ ID NO: 1, an oligodeoxynucleotide including a sequence as set forth as SEQ ID NO: 8, and an oligodeoxynucleotide including a sequence as set forth as SEQ ID NO: 20. Another specific non-limiting example is a composition that includes an oligodeoxynucleotide including a sequence as set forth as SEQ ID NO: 1, an oligodeoxynucleotide including a sequence as set forth as SEQ ID NO: 20, and an oligodeoxynucleotide including a sequence as set forth as SEQ ID NO: 108. Yet another specific non-limiting example is a composition that includes an oligodeoxynucleotide including a sequence as set forth as SEQ ID NO: 1, an oligodeoxynucleotide including a sequence as set forth as SEQ ID NO: 7, and an oligodeoxynucleotide including a sequence as set forth as SEQ ID NO: 108. A further specific non-limiting example is a composition that includes an oligodeoxynucleotide including a sequence as set forth as SEQ ID NO: 7, an oligodeoxynucleotide including a sequence as set forth as SEQ ID NO: 20, and an oligodeoxynucleotide including a sequence as set forth as SEQ ID NO: 98. Another specific, non-limiting example is a composition that includes an oligodeoxynucleotide including a sequence as set forth as SEQ ID NO: 20, an oligodeoxynucleotide including a sequence as set forth as SEQ ID NO: 98, and including an oligodeoxynucleotide having a sequence as set forth as SEQ ID NO: 108. Yet another specific, non-limiting example is a composition that includes an oligodeoxynucleotide including a sequence as set forth as SEQ ID NO: 1, an oligodeoxynucleotide including a sequence as set forth as SEQ ID NO: 7, and an oligodeoxynucleotide including a sequence as set forth as SEQ ID NO: 20.

IID Type ODNs

D type ODNs differ both in structure and activity from K type ODNs. The unique activities of D type ODNs are disclosed below (see section C). For example, as disclosed herein, D oligodeoxynucleotides stimulate the release of cytokines from cells of the immune system. In specific, non-limiting examples D type oligodeoxynucleotides stimulate the release or production of IFN-α by monocytes and/or plasmacitoid dendritic cells and the release or production of IFN-γ by NK cells. The stimulation of NK cells by D oligodeoxynucleotides can be either direct or indirect.

With regard to structure, in one embodiment, a CpG motif in a D type oligodeoxynucleotides has been described by Formula II:

wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D ODN.

In one embodiment, a D type ODN is at least about 16 nucleotides in length and includes a sequence represented by Formula III:

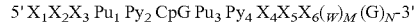

wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1$ $Py_2$ CpG $Pu_3$ $Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN these nucleotides are termed the 5' far flanking region. Nucleotides 3' of $X_4X_5X_6$ in the D ODN are termed the 3' far flanking region.

In one specific non-limiting example, $Py_2$ is a cytosine. In another specific, non-limiting example, $Pu_3$ is a guanidine. In yet another specific, non limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific non-limiting example, N is from about 4 to about 8. In another specific, non-limiting example, N is about 6.

D-type CpG oligodeoxynucleotides can include modified nucleotides. Without being bound by theory, modified nucleotides can be included to increase the stability of a D-type oligodeoxynucleotide. Without being bound by theory, because phosphorothioate-modified nucleotides confer resistance to exonuclease digestion, the D ODN are "stabilized" by incorporating phosphorothioate-modified nucleotides. In one embodiment, the CpG dinucleotide motif and its immediate flanking regions include phosphodiester rather than phosphorothioate nucleotides. In one specific non-limiting example, the sequence $Pu_1$ $Py_2$ CpG $Pu_3$ $Py_4$ includes phosphodiester bases. In another specific, non-limiting example, all of the bases in the sequence $Pu_1$ $Py_2$ CpG $Pu_3$ $Py_4$ are phosphodiester bases. In yet another specific, non-limiting example, $X_1X_2X_3$ and $X_4X_5X_6(W)_M$ $(G)_N$ include phosphodiester bases. In yet another specific, non-limiting example, $X_1X_2X_3$ $Pu_1$ $Py_2$ CpG $Pu_3$ $Py_4$ $X_4X_5X_6(W)_M$ $(G)_N$ include phosphodiester bases. In further non-limiting examples the sequence $X_1X_2X_3$ includes at most one or at most two phosphothioate bases and/or the sequence $X_4X_5X_6$ includes at most one or at most two phosphothioate bases. In additional non-limiting examples, $X_4X_5X_6(W)_M$ $(G)_N$ includes at least 1, at least 2, at least 3, at least 4, or at least 5 phosphothioate bases. Thus, a D type oligodeoxynucleotide can be a phosphorothioate/phosphodiester chimera.

As disclosed herein, any suitable modification can be used in the present invention to render the ODNs resistant to degradation in vivo (e.g., via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D type oligodeoxynucleotides can also be modified to contain a secondary structure (e.g., stem loop structure). Without being bound by theory, it is believed that incorporation of a stem loop structure renders and oligodeoxynucleotide more effective.

In a further embodiment, $Pu_1\,Py_2$ and $Pu_3\,Py_4$ are self-complementary. In another embodiment, $X_1X_2X_3$ and $X_4X_5X_6$ are self-complementary. In yet another embodiment $X_1X_2X_3Pu_1\,Py_2$ and $Pu_3\,Py_4\,X_4X_5X_6$ are self-complementary.

In one embodiment, the D type oligodeoxynucleotides disclosed herein are at least about 16 nucleotides in length. In a second embodiment, a D type oligodeoxynucleotide is at least about 18 nucleotides in length. In another embodiment, a D type oligodeoxynucleotide is from about 16 nucleotides in length to about 100 nucleotides in length. In yet another embodiment, a D type oligodeoxynucleotide is from about 16 nucleotides in length to about 50 nucleotides in length. In a further embodiment, a D type oligodeoxynucleotide is from about 18 nucleotides in length to about 30 nucleotides in length.

In another embodiment, the oligodeoxynucleotide is at least 18 nucleotides in length, and at least two G's are included at the 5' end of the molecule, such that the oligodeoxynucleotide includes a sequence represented by Formula IV:

$$5'\,GGX_1X_2X_3\,Pu_1\,Py_2\,CpG\,Pu_3\,Py_4\,X_4X_5X_6(W)_M(G)_N\text{-}3'.$$

The D type oligodeoxynucleotide can include additional G's at the 5' end of the oligodeoxynucleotide. In one specific example, about 1 or about 2 G's are included at the 5' end of an oligodeoxynucleotide including a sequence as set forth as Formula IV.

Specific, non-limiting examples of D type ODNs can be found in U.S. patent application Ser. No. 10/068,160, which is herein incorporated by reference. Specific, non-limiting examples of D and K type ODN, as disclosed herein, can be found in Verthelyi et al., *J. Immunol.* 166:2372-2377, 2001, which is herein incorporated by reference.

Thus disclosed herein is an oligodeoxynucleotide composition including at least two oligodeoxynucleotide of at least about 10 nucleotides in length, wherein the oligodeoxynucleotides comprise an unmethylated CpG motif and at least one of the oligodeoxynucleotides has a sequence represented by the formula 5' RY-CpG-RY 3', wherein R is A or G and Y is C or T. In addition, the oligodeoxynucleotides differ in their nucleic acid sequence. Also disclosed are oligodeoxynucleotide compositions including at least three, or at least four, different D type ODN.

In one embodiment, at least one of the oligodeoxynucleotides is at least about 16 nucleotides in length and includes a sequence represented by the following formula:

$$5'\,X_1X_2X_3\,Pu_1\,Py_2\,CpG\,Pu_3\,Py_4\,X_4X_5X_6(W)_M(G)_N\text{-}3'$$

wherein the central CpG motif is unmethylated, Pu is a purine nucleotide, Py is a pyrimidine nucleotide, X and W are any nucleotide, M is any integer from 0 to 10, and N is any integer from 4 to 10. These compositions are of use in stimulating an immune response.

In one specific, non-limiting example is a composition that includes an oligodeoxynucleotide including a sequence as set forth as SEQ ID NO: 32, an oligodeoxynucleotide including a sequence as set forth as SEQ ID NO: 106, and an oligodeoxynucleotide including a sequence as set forth as SEQ ID NO: 40. Another specific, non-limiting example is a composition that includes an oligodeoxynucleotide including a sequence as set forth as SEQ ID NO: 32, an oligodeoxynucleotide including a sequence as set forth as SEQ ID NO: 106, and an oligodeoxynucleotide including a sequence as set forth as SEQ ID NO: 102. Yet another specific, non-limiting example is a composition that includes an oligodeoxynucleotide including a sequence as set forth as SEQ ID NO: 32, an oligodeoxynucleotide including a sequence as set forth as SEQ ID NO: 42, and an oligodeoxynucleotide including a sequence as set forth as SEQ ID NO: 40.

The oligodeoxynucleotides (both K and D type) disclosed herein can be synthesized de novo using any of a number of procedures well known in the art. For example, the oligodeoxynucleotides can be synthesized as set forth in U.S. Pat. No. 6,194,388, which is herein incorporated by reference in its entirety. A oligodeoxynucleotide including a CpG motif can be synthesized using, for example, the B-cyanoethyl phophoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

Delivery Complexes and Pharmaceutical Compositions

In one embodiment, multiple K type or D type oligodeoxynucleotides (ODN) including a CpG motif are included in a delivery complex. The delivery complex can include the multiple different ODN (e.g. at least two different ODNs, at least three different ODNs, or at least four different ODNs) and a targeting agent. A targeting agent is any agent that can be used to increase the delivery of an ODN to a cell. The cell can be any cell, including, but not limited to an antigen presenting cell, a dendritic cell, a B cell or a T cell. Any suitable targeting agent can be used.

For example, one or more of the oligodeoxynucleotides can be associated with (e.g., ionically or covalently bound to, or encapsulated within) a targeting agent. A variety of coupling or cross-linking agents can be used to form the delivery complex, such as protein A, carbodiamide, and N-succinimidyl-3-(2-pyridyldithio)propionate (SPDP). Examples of oligodeoxynucleotide delivery complexes include an oligodeoxynucleotide associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the oligodeoxynucleotide is released in a functional form at the target cells.

In one embodiment, a pharmacological composition is provided that includes at least two oligodeoxynucleotides and a pharmacologically acceptable carrier. Pharmacologically acceptable carriers (e.g., physiologically or pharmaceutically acceptable carriers) are well known in the art. A suitable pharmacological composition can be formulated to facilitate the use of a K type ODN or D type ODN in vivo and/or ex vivo. Such a composition can be suitable for delivery of the active ingredient to any suitable host, such as a patient or other subject for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use can be formulated in a conventional manner using one or more pharmacologically (e.g., physiologically or pharmaceutically) acceptable carriers including excipients, as well as optional auxiliaries that facilitate processing of the active compounds into preparations which can be used pharmaceutically. Proper formulation is dependent upon the route of administration chosen, and whether use will be an in vivo or an ex vivo use. For use in vivo, administration can be either systemic or local. In addition, one of skill in the art can readily select a suitable route of administration, including, but not limited to intravenous, intramuscular, intraperitoneal, transmucosal, subcutaneous, transdermal, transnasal, and oral administration.

Thus, for injection, at least two ODNs including a CpG motif can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Similarly, D type or K type oligodeoxynucleotides can be formulated for intratracheal administration or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

Compositions that Include Multiple K Type or Multiple D Type ODN and Their Use in Inducing an Immune Response Compositions including multiple different ODN can be administered to a subject to induce an immune response. The administration of the multiple different oligodeoxynucleotides can be by any suitable method. For example, the ODNs can be administered in vivo or ex vivo. The subject can be any mammal, particularly a primate, such as a human.

In one embodiment, the compositions are of use in inducing an immune response in a subject. A substantial "induction" or an "increase" in an immune response can be, for example, at least an about 50%, 75%, 90%, 100%, 200%, 300%, or 500% increase in a single parameter of an immune response. In one embodiment, administration of a composition including multiple different ODNs that include a CpG motif results in a substantial increase in a single parameter of an immune response as compared to administration of one of the ODNs of the composition. In another embodiment, administration of a composition that includes multiple different ODNs including a CpG motif results in a substantial increase in two or more parameters of an immune response as compared to administration of one of the ODNs of the composition. In a further embodiment, administration of the composition including multiple different ODNs with a CpG motif increases more parameters of the immune response than the administration of only one of the ODNs of the composition. Thus, administration of multiple different ODNs with a CpG motif broadens the immune response in a subject as compared to administration of a single ODN.

In another embodiment, the compositions disclosed herein are of use in inducing an immune response a large percentage of the individuals in a population. Thus, in one embodiment, upon administration of the multiple oligodeoxynucleotides to a population of subjects, at least about 80%, at least about 90%, at least about 95%, at least about 98%, or at least about 99%, of the individuals in the population produce an immune response. In one embodiment, following administration of the multiple different oligodeoxynucleotides to a population of subjects, at least about 80% of the subjects produce an immune response. In one embodiment, the immune response includes substantial stimulation of a single parameter of the immune response as compared to administration of only one of the oligodeoxynucleotides to the population of subjects. In another embodiment, the immune response includes substantial stimulation of two or more parameters of the immune response as compared to administration of only one of the oligodeoxynucleotides to the population of subjects. In another embodiment, upon administration of the multiple different oligodeoxynucleotides to a population of subjects, at least two parameters of the immune response are stimulated in the subjects, wherein administration of only one of the oligodeoxynucleotides of the composition to the population of subjects stimulates only a single parameter of the immune response.

In order to induce an immune response, the multiple different ODNs including a CpG motif can be administered either alone or in conjunction with another molecule. Co-administration includes administering the molecule and the multiple different ODNs including the CpG motif at the same time, or sequentially, for example, substantially contemporaneously, with the other molecule. The other molecule can be any other agent, such as a protein, an antigenic epitope, a hydrocarbon, lipid, mitogen, an anti-infectious agent (such as antiviral, antifungal, or anti-bacterial agent) a anti-neoplastic agent, or a vaccine (such as a live, attenuated, or heat-killed vaccine).

In one embodiment, at least two different ODNs including a CpG motif are administered to a subject, such as a subject that has an autoimmune disease. Specific, non-limiting examples of autoimmune diseases include, but are not limited to diabetes, rheumatoid arthritis, lupus erythematosus, and multiple sclerosis.

Also disclosed herein are methods of use to treat, prevent, or ameliorate an allergic reaction in a subject. An allergy refers to an acquired hypersensitivity to a substance (i.e., an allergen). Allergic conditions include eczema, allergic rhinitis or coryza, hay fever, bronchial asthma, uticaria (hives), food allergies, and other atopic conditions. The list of allergens is extensive and includes pollens, insect venoms, animal dander, dust, fungal spores, and drugs (e.g., penicillin). Examples of natural, animal, and plant allergens can be found in International Patent Application WO 98/18810. In one embodiment at least two different oligodeoxynucleotides including a CpG motif are administered to a subject to treat an allergic condition such as allergic asthma. In another embodiment, the ODNs are administered in combination with any suitable anti-allergenic agent. Suitable anti-allergenic agents include those substances given in treatment of the various allergic conditions described above, examples of which can be found in the Physicians' Desk Reference (1998).

In another embodiment, at least two different ODNs including a CpG motif are administered to a subject that has a neoplasm. The ODNs are administered either alone or in combination with any suitable anti-neoplastic agent, such as a chemotherapeutic agent or radiation. Suitable neoplasms include, but are not limited to, solid tumors such as cancers of the brain, lung (e.g., small cell and non-small cell), ovary, breast, prostate, and colon, as well as carcinomas and sarcomas. Without being bound by theory, it is believed that the ODNs increase the immune response to the neoplasm, and thus are involved in the reduction of tumor burden.

In a further embodiment, a method is provided to enhance the efficacy of any suitable vaccine. Suitable vaccines include those directed against Leishmania, Hepatitis A, B, and C, examples of which can be found in the Physicians' Desk Reference (1998), and DNA vaccines directed against, for example, HIV and malaria. (See generally Klinman et al., 17 *Vaccine* 17:19 (1999); McCluskie and Davis, *J. Immun.* 161: 4463 (1998)).

Multiple different ODNs including a CpG motif can be used to treat, prevent, or ameliorate any condition associated with an infectious agent. The multiple different ODNs can be administered to a subject infected with the infectious agent alone or in combination with any suitable anti-infectious agent, such as an antiviral, anti-fungal or anti-bacterial agent (see Physicians' Desk Reference, 1998). Specific, non-limiting examples of infectious agents, and conditions associated with infectious agents are tularemia, francisella, schistosomiasis, tuberculosis, malaria, and leishmaniasis. Examples of infectious agents such as viruses, bacteria, fungi, and other organisms (e.g., protists) can be found in International Patent Application WO 98/18810.

Compositions including multiple ODNs with CpG motifs can be used to an immune response in combination with any suitable antisense therapy. Suitable antisense agents are those that bind either with DNA or RNA and block their function by inhibiting expression of the sequence to which the antisense agents are bound. See generally Lonnberg et al., 28 *Ann. Med.* 511 (1996); Alama et al., 36 *Pharmacol. Res.* 171 (1997); Scanlon et al., 9 *FASEB J.* 1288 (1995), amongst others.

The methods disclosed herein for inducing an immune response can be used to treat, prevent, or ameliorate the symptoms resulting from exposure to a bio-warfare agent. Suitable bio-warfare agents include those naturally occurring biological agents that have been specifically modified in the laboratory. Often, modification of these agents has altered them such that there is no known treatment. Examples include Ebola, Anthrax, and Listeria. In the course of ameliorating the symptoms after exposure, administration of multiple ODNs including a CpG motif may not cure the patient, but rather can extend the patient's life sufficiently such that some other treatment can then be applied.

In one embodiment the different ODNs are K type ODN and a parameter of the humoral immune response is substantially increased in the subject. Parameters of the humoral immune response include, but are not limited to, IgM production, Il-6 production, and/or proliferation. In one embodiment, the multiple different ODN are K type ODN and the immune response is a humoral immune response. Thus, in one embodiment, the immune response comprises proliferation of peripheral blood mononuclear cells, IgM production, IL-6 production, or a combination thereof. Thus, in one specific, non-limiting example, K type ODN can be selected such that administration of the combination of K type ODN causes increased production of IL-6 in a at least about 80%, at least about 90%, at least about 95%, at least about 98%, or at least about 99%, of the individuals in the population produces an immune response.

In another embodiment, multiple different D type ODNs are used to produce a substantial immune response in a subject. Administration of a D type oligodeoxynucleotide activates monocytes and/or natural killer cells, and induces the maturation of dendritic cells. Furthermore, a D type oligodeoxynucleotide can be used to increase the production of cytokines (for example IP-10, IFN-α or IFN-γ) by a cell of the immune system.

In one embodiment, a method is provided for inducing an immune response in a subject wherein the method includes contacting a monocyte or a dendritic cell precursor in vitro with multiple different D type ODNs to produce an activated antigen presenting cell. The monocytes or dendritic cell precursors can be contacted with the D type ODNs in the presence of or in the absence of antigen. The activated antigen presenting cell is then administered to the subject to induce an immune response.

In another embodiment, a method is provided herein for inducing an immune response in a subject that includes contacting a monocyte or a dendritic cell precursor in vitro with a D type ODNs to produce an activated antigen presenting cell. The monocytes or dendritic cell precursors can be contacted with the D type ODNs in the presence of or in the absence of antigen. Lymphocytes or natural killer are then contacted with the activated antigen presenting cells in vitro, or with cytokines secreted by the activated antigen presenting cells in vitro, to produce activated lymphocytes or activated natural killer cells. The activated lymphocytes or natural killer cells are then administered to the subject to induce the immune response. In yet another embodiment, an immunoregulatory response is induced.

This disclosure is illustrated by the following non-limiting Examples.

EXAMPLES

Example 1

The following example demonstrates the varied immune response induced in vitro in different donors after administration of an ODN including a single CpG sequence. Induction of an immune response was measured by production of the cytokines IL-6 and IFN-γ, and cell proliferation in human peripheral blood mononuclear cells (PBMC) isolated from individual donors.

PBMC were isolated, as described elsewhere (Ballas et al., 85 *J. Allergy Clin. Immunol.* 453 (1990); Ballas et al., 45 1039 (1990); Ballas et al., 150 *J. Immunol.* 17 (1993)). ODNs were synthesized on a DNA synthesizer (Applied Biosystems Inc., Foster City, Calif.), as described elsewhere (Beacage and Caruthers, "Deoxynucleoside Phosphoramidites-A New Class of Key Intermediates for Deoxypolynucleotide Synthesis," 22 *Tetrahedron Letters* 1859 (1981)). In some ODNs, the normal DNA backbone phosphodiesterase linkages were replaced with phosphorothioate linkages, as described elsewhere (Agrawal et al., 94 *Proc. Natl. Acad. Sci. USA* 2620 (1997); Agrawal 14 *TIB TECH* 376 (1996)). To reduce degradation of the ODNs, those that did not have an entire phosphorothioate backbone contained phosphorothioate linkages at the 5' and 3' ends. Cells were incubated for approximately 72 hours with the various ODNs. IL-6 and IFN-γ levels were determined by ELISA using anti-IL-6 and anti-IFN-γ antibodies, as described elsewhere (Maniatis et al., *Molecular Cloning: A Laboratory Manual*, Cold Spring Harbor Laboratory Press, New York, 1989). Cell proliferation was determined by [$^3$H] thymidine incorporation, as described elsewhere (Liang et al., 98 *J. Clin. Invest.* at 1121). IL-6 levels are set forth in Table 1: Induction of an Immune Response (IL-6); IFN-γ levels are set forth in Table 5: Induction of an Immune Response (IFN-γ); and cell proliferation is set forth in Table 6: Induction of an Immune Response (Cell Proliferation).

Example 2

The following example demonstrates in vitro induction of an immune response after administration of an ODN that includes a CpG sequence. In a population of subjects, only some of the subjects mounted an immune response to each individual ODN. Induction of an immune response was measured by production of the cytokines IL-6 and IFN-γ, and cell proliferation in human PBMC isolated from individual donors.

Human PBMC were isolated, as described in Example 1. ODNs were synthesized on a DNA synthesizer (Applied Biosystems Inc., Foster City, Calif.), as described in Example 1.

TABLE 1

Induction of an Immune Response (IL-6)

| | 3 | 4 | 7 | 8 | 15 | 16 | 17 | 18 | 19 | 23 | 24 | 25 | 26 | 27 |
|---|---|---|---|---|---|---|---|---|---|---|---|---|---|---|
| | | | | | | | IL-6 | | | | | | | |
| SEQ ID NO: 1 | 35 | 53 | 19 | 12 | 9 | 2 | 8 | 6 | 33 | 15 | 5 | 40 | 13 | 3 |
| SEQ ID NO: 18 | 2 | 3 | 25 | 65 | — | — | — | — | — | 8 | 3 | 3 | 1 | 1 |
| SEQ ID NO: 20 | 50 | 45 | 9 | 43 | 5 | 9 | 20 | 20 | 20 | — | 12 | 57 | 13 | 3 |
| SEQ ID NO: 98 | 18 | 42 | 9 | 41 | 60 | 80 | 25 | 11 | 22 | 17 | 6 | 12 | 2 | 1 |
| SEQ ID NO: 105 | — | — | — | — | — | — | — | — | — | 13 | 7 | 16 | 3 | 1 |

TABLE 2

Induction of an Immune Response (IFN-γ)

| | 3 | 4 | 5 | 9 | 13 | 14 | 15 | 17 |
|---|---|---|---|---|---|---|---|---|
| | | | | IFN-γ (ELISA) | | | | |
| SEQ ID NO: 40 | 154 | 64 | 6 | 2 | 5 | 11 | 15 | 3 |
| SEQ ID NO: 42 | 92 | 56 | 419 | 28 | 8 | 4 | 4 | 8 |
| SEQ ID NO: 43 | 13 | 3 | 269 | 93 | 15 | 6 | 5 | 8 |
| SEQ ID NO: 100 | 22 | 2 | 16 | 2 | 9 | 9 | 9 | 6 |
| SEQ ID NO: 101 | 3 | 2 | 15 | 25 | 0 | 16 | 5 | 5 |
| SEQ ID NO: 102 | — | — | 0 | 1 | 60 | 250 | 6 | 3 |
| SEQ ID NO: 103 | — | — | 4 | 1 | 3 | 2 | 8 | 5 |
| SEQ ID NO: 104 | — | — | 4 | 1 | 2 | 1 | 3 | 4 |

TABLE 3

Induction of an Immune Response (Cell Proliferation)

| | 1 | 2 | 3 | 4 | 20 | 21 | 22 |
|---|---|---|---|---|---|---|---|
| | | | | Proliferation ([$^3$H] T) | | | |
| SEQ ID NO: 1 | 22 | 36 | 33 | 9 | 18 | 15 | 14 |
| SEQ ID NO: 9 | 5 | 17 | 16 | 11 | 18 | 18 | 13 |
| SEQ ID NO: 10 | 9 | 10 | 20 | 25 | 14 | 23 | 12 |
| SEQ ID NO: 12 | 6 | 8 | 10 | 19 | 4 | 7 | 6 |
| SEQ ID NO: 15 | 9 | 47 | 11 | 13 | 14 | 17 | 12 |
| SEQ ID NO: 31 | 2 | 15 | 10 | 16 | 6 | 8 | 7 |
| SEQ ID NO: 45 | 3 | 7 | 16 | 15 | 10 | 16 | 10 |
| SEQ ID NO: 50 | 3 | 6 | 10 | 9 | 6 | 6 | 5 |
| SEQ ID NO: 54 | 4 | 5 | 10 | 9 | 5 | 5 | 4 |

The foregoing data demonstrates induction of an immune response, to an ODN that includes various sequences, in human PBMC isolated from individual donors. Specifically, these data demonstrate that a single ODN sequence induces a varied immune response in different donors. For example, in Table 4, an ODN including SEQ ID NO: 98 induced IL-6 levels ranging from 2 to 80, in Table 5, an ODN including SEQ ID NO: 42 induced IFN-γ levels ranging from 4 to 419, and in Table 6, an ODN including SEQ ID NO: 15 induced cell proliferation ranging from 9 to 47.

In some ODNs, the normal DNA backbone phosphodiesterase linkages were replaced with phosphorothioate linkages, as described in Example 1. To reduce degradation of the ODNs, those that did not have an entire phosphorothioate backbone contained phosphorothioate linkages at the 5' and 3' ends. Cells were incubated for approximately 72 hours with the various ODNs. IL-6 and IFN-γ levels were determined by ELISA using anti-IL-6 and anti-IFN-γ antibodies, as described in Example 1. Cell proliferation was determined by [$^3$H] thymidine incorporation, as described in Example 1. Results are set forth in Table 4: Induction of an Immune Response to Multiple ODNs.

TABLE 4

Percent Induction of an Immune Response (IL-6)

| | Percent Induction | Number of Donors |
|---|---|---|
| SEQ ID NO: 1 | 69% | 26 |
| SEQ ID NO: 109 | 67% | 9 |
| SEQ ID NO: 20 | 65% | 34 |
| SEQ ID NO: 7 | 49% | 39 |
| SEQ ID NO: 108 | 47% | 38 |
| SEQ ID NO: 98 | 44% | 39 |
| SEQ ID NO: 110 | 30% | 10 |
| SEQ ID NO: 111 | 26% | 19 |
| SEQ ID NO: 112 | 7% | 29 |

TABLE 5

Percent Induction of an Immune Response (IFN-γ)

| | Percent Induction | Number of Donors |
|---|---|---|
| SEQ ID NO: 43 | 93% | 42 |
| SEQ ID NO: 42 | 91% | 23 |
| SEQ ID NO: 106 | 87% | 23 |
| SEQ ID NO: 32 | 82% | 17 |
| SEQ ID NO: 40 | 79% | 19 |
| SEQ ID NO: 103 | 58% | 12 |
| SEQ ID NO: 102 | 57% | 28 |

TABLE 5-continued

Percent Induction of an Immune Response (IFN-γ)

| | Percent Induction | Number of Donors |
|---|---|---|
| SEQ ID NO: 107 | 10% | 31 |
| SEQ ID NO: 68 | 11% | 19 |

TABLE 6

Heterogeneity in Induction of an Immune Response (IL-6)

| | 1 | 2 | 3 | 4 | 5 | 6 | 7 | 8 |
|---|---|---|---|---|---|---|---|---|
| SEQ ID NO: 20 | -- | ++ | + | + | + | + | ++ | ++ |
| SEQ ID NO: 7 | + | + | + | -- | ++ | + | ++ | + |
| SEQ ID NO: 1 | ++ | ++ | + | -- | + | + | ++ | -- |

TABLE 7

Heterogeneity in Induction of an Immune Response (IFN-γ)

| | 1 | 2 | 3 | 4 | 5 | 6 | 7 | 8 |
|---|---|---|---|---|---|---|---|---|
| SEQ ID NO: 40 | ++ | ++ | -- | -- | -- | + | ++ | + |
| SEQ ID NO: 32 | + | ++ | + | + | ++ | + | -- | -- |
| SEQ ID NO: 102 | -- | -- | ++ | ++ | ++ | + | -- | ++ |

The foregoing data demonstrates induction of an immune response to an
ODN including a CpG motif in human PBMC isolated from individual donors. Specifically, these data demonstrate that a single sequence induces a varied immune response in different donors, as shown, e.g., in Table 4, the percent of donors induced varied from 7% to 69%, as measured by IL-6 production, and in Table 5, the percent of donors induced varied from 11% to 93%, as measured by IFN-γ production. Further, as demonstrated in Tables 6 and 7, there was substantial heterogeneity in induction of an immune response in different donors.

The foregoing data demonstrates the induction of an immune response after administration of multiple different ODNs that include various CpG sequences in human PBMC isolated from individual donors. Specifically, these data demonstrate that multiple ODNs synergistically induce an immune response, as demonstrated by, e.g., an increase of 26.6% as measured by cell proliferation, 29.6% as measured by IL-6 levels, and 71.7% as measured by IFN-γ levels after administration to Donor 1. Combination of an ODN that includes SEQ ID NO: 1 and an ODN that includes SEQ ID NO: 43 produced this enhanced immune response compared to the combined immune response of each ODN administered separately.

Example 4

The following example demonstrates in vitro induction of an immune response after administration of multiple different ODNs that include a CpG sequence. The induced immune response was measured by increased IFN-γ in human PBMC isolated from individual donors as compared to unstimulated PBMC from the same donor.

Human PBMC were isolated, as described in Example 1. ODNs were synthesized on a DNA synthesizer (applied Biosystems Inc., Foster City, Calif.), as described in Example 1. In some ODNs, the normal DNA backbone phosphodiesterase linkages were replaced with phosphorothioate linkages, as described in Example 1. To induce degradation of the ODNs, those that did not have an entire phosphorothioate backbone contained phosphorothioate linkages at the 5' and 3' ends. Cells were incubated for approximately 72 hours with the various ODNs. IL-6 and IFN-γ levels were determined by ELISA using anti-IL-6 and anti-IFN-γ antibodies, as described in Example 1. The percentages of donors induced by the combination of different ODNs by at least 3-fold for IL-6 and 5-fold for IFN-γ are set forth for IL-6 levels in Table 9: Percent Induction of an Immune Response (IL-6) and for IFN-γ levels in Table 10: Induction of an Immune Response (IFN-γ).

Example 3

The following example demonstrates in vitro induction of an immune response after administration of multiple ODNs, each of which includes a different CpG sequence. Induction of an immune response was measured by production of the cytokines IL-6 and IFN-γ, and cell proliferation in human PBMC isolated from individual donors.

Human PBMC were isolated, as described in Example 1. ODNs were synthesized on a DNA synthesizer (Applied Biosystems Inc., Foster City, Calif.), as described in Example 1. In some ODNs, the normal DNA backbone phosphodiesterase linkages were replaced with phosphorothioate linkages, as described in Example 1. To reduce degradation of the ODNs, those that did not have an entire phosphorothioate backbone contained phosphorothioate linkages at the 5' and 3' ends. Cells were incubated for approximately 72 hours with the various ODNs. IL-6 and IFN-γ levels were determined by ELISA using anti-IL-6 and anti-IFN-γ antibodies, as described in Example 1. Cell proliferation was determined by [$^3$H] thymidine incorporation, as described in Example 1. Results are set forth in Table 8: Induction of an Immune Response to Multiple Different ODNs.

TABLE 8

Induction of an Immune Response to Multiple Different ODNs

| | IL-6 (ELISA) | IFN-γ (ELISA) | Proliferation ([$^3$H] T) |
|---|---|---|---|
| Donor 1 | | | |
| SEQ ID NO: 1 | 12.0 | 2.3 | 13.0 |
| SEQ ID NO: 43 | 7.0 | 9.0 | 1.6 |
| SEQ ID NO: 1 + SEQ ID NO: 43 | 27 | 40.0 | 19.9 |
| Donor 2 | | | |
| SEQ ID NO: 1 | 5.0 | 13.0 | 37.7 |
| SEQ ID NO: 43 | 2.0 | 7.0 | 1.3 |
| SEQ ID NO: 1 + SEQ ID NO: 43 | 9.0 | 33.0 | 68.6 |
| Donor 3 | | | |
| SEQ ID NO: 1 | 10.0 | 8.0 | 13.1 |
| SEQ ID NO: 43 | 1.0 | 12.0 | 1.3 |
| SEQ ID NO: 1 + SEQ ID NO: 43 | 8.0 | 42.0 | 17.5 |

TABLE 9

Percent Induction of an Immune Response (IL-6) to Multiple ODNs

| | Percent Induction | Number of Donors |
|---|---|---|
| SEQ ID NO: 7 + SEQ ID NO: 1 + SEQ ID NO: 108 | 100% | 4 |

TABLE 9-continued

Percent Induction of an Immune Response
(IL-6) to Multiple ODNs

| | Percent Induction | Number of Donors |
|---|---|---|
| SEQ ID NO: 7 + SEQ ID NO: 20 + SEQ ID NO: 98 | 100% | 2 |
| SEQ ID NO: 20 + SEQ ID NO: 108 + SEQ ID NO: 98 | 100% | 2 |
| SEQ ID NO: 7 + SEQ ID NO: 20 + SEQ ID NO: 1 | 80% | 5 |
| SEQ ID NO: 20 + SEQ ID NO: 1 + SEQ ID NO: 108 | 80% | 5 |
| SEQ ID NO: 7 + SEQ ID NO: 20 + SEQ ID NO: 108 | 60% | 10 |
| SEQ ID NO: 7 + SEQ ID NO: 108 + SEQ ID NO: 98 | 38% | 16 |

TABLE 10

Percent Induction of an immune Response
(IFN-γ) to Multiple ODNs

| | Percent Induction | Number of Donors |
|---|---|---|
| SEQ ID NO: 43 + SEQ ID NO: 40 + SEQ ID NO: 106 | 100% | 5 |
| SEQ ID NO: 32 + SEQ ID NO: 40 + SEQ ID NO: 106 | 100% | 5 |
| SEQ ID NO: 43 + SEQ ID NO: 102 + SEQ ID NO: 106 | 89% | 19 |
| SEQ ID NO: 32 + SEQ ID NO: 40 + SEQ ID NO: 42 | 80% | 5 |
| SEQ ID NO: 32 + SEQ ID NO: 102 + SEQ ID NO: 106 | 40% | 5 |
| SEQ ID NO: 43 + SEQ ID NO: 40 + SEQ ID NO: 42 | 40% | 5 |

The foregoing data demonstrates the induction of an immune response after administration of multiple ODNs including various CpG sequences in human PBMC isolated from individual donors. Specifically, these data demonstrate that administration of multiple different ODNs synergistically induces an immune response, as demonstrated by, e.g., Table 9, in which the percent induction was increased in two of the multiple ODNs to 100%, as measured by IL-6 production. This is also shown in Table 10, in which the percent induction was increased to 100% for three of the multiple ODNs, as measured by IFN-γ production.

Example 5

The following example demonstrates in vitro induction of an immune response after administration of a single ODN including multiple different CpG sequences. Induction of an immune response was measured by production of the cytokines IL-6 and IFN-γ, and cell proliferation in human PBMC isolated from individual donors.

Human PBMC were isolated, as described in Example 1. ODNs were synthesized on a DNA synthesizer (Applied Biosystems Inc., Foster City, Calif.), as described in Example 1. In some ODNs, the normal DNA backbone phosphodiesterase linkages were replaced with phosphorothioate linkages, as described in Example 1. To reduce degradation of the ODNs, those that did not have an entire phosphorothioate backbone were provided with phosphorothioate linkages at the 5' and 3' ends. Cells were incubated for approximately 72 hours with the various ODNs. IL-6 and IFN-γ levels were determined by ELISA using anti-IL-6 and anti-IFN-γ antibodies, as described in Example 1. Cell proliferation was determined by [$^3$H] thymidine incorporation, as described in Example 1. Results are set forth in Table 11: Induction of an Immune Response to a Single ODN Including Multiple Different CpG Sequences.

TABLE 11

Induction of an Immune Response to a Single ODN
Including Multiple Different CpG Sequences

| | IL-6 (ELISA) | IFN-γ (ELISA) | Proliferation ([$^3$H] T) |
|---|---|---|---|
| Donor 1 | | | |
| SEQ ID NO: 1 | 5 | 3 | 18 |
| SEQ ID NO: 43 | 3 | 4 | 3 |
| SEQ ID NO: 1 + SEQ ID NO: 43 | 23 | 7 | 29 |
| Donor 2 | | | |
| SEQ ID NO: 1 | 5 | 3 | 31 |
| SEQ ID NO: 43 | 2 | 4 | 4 |
| SEQ ID NO: 1 + SEQ ID NO: 43 | 15 | 6 | 57 |

The foregoing data demonstrates the induction of an immune response after administration of a single ODN including multiple different CpG sequences in human PBMC isolated from individual donors. Specifically, these data demonstrate that a single ODN that includes multiple different CpG sequences synergistically induces an immune response, such as is demonstrated by, e.g., an increase in IL-6 levels of 65.2% in Donor 1 and 53.3% in Donor 2 after administration of a single ODN that includes SEQ ID NO: 1 and SEQ ID NO: 43, compared to the combined immune response of a single ODN that includes either SEQ ID NO: 1 or SEQ ID NO: 43 when administered separately.

Example 6

Over 100 CpG ODNs were then screened for their ability to stimulate PBMC from a diverse pool of normal donors (Table 12).

TABLE 12

Characteristics of the PBMC Donor Pool*

| Characteristic | Percent of donor population |
|---|---|
| Sex | |
| Male | 72 |
| Female | 28 |
| Race | |
| White | 70 |
| Black | 28 |
| Hispanic | 2 |
| Age (years) | |
| Range | 23-66 |
| Average | 40 ± 11 |

*Characteristics of the donor pool from which PBMC samples were randomly derived.

Eleven of the most stimulatory ODNs were then tested for their ability to stimulate IL6, IgM, Proliferation, or all three responses simultaneously, on PBMC from over 100 donors (Table 13).

TABLE 13: Oligodeoxynucleotide Sequences

Sequences of phosphorothioate ODNs included in this example. CpG dinucleotides are underlined. K3 is SEQ ID NO: 20, K19 is SEQ ID NO: 7, K23 is SEQ ID NO: 1, K82 is SEQ ID NO: 113, K83 is SEQ ID NO: 114, K84 is SEQ ID NO: 115, K85 is SEQ ID NO: 116, K89 is SEQ ID NO: 109, K109 is SEQ ID NO: 117, K110 is SEQ ID NO: 98, K123 is SEQ ID NO: 108, and K121 is SEQ ID NO: 112.

| Name | Sequence* |
|---|---|
| CpG ODN (K type) | |
| K3 | A T C G A C T C T C G A G C G T T C T C |
| K19 | A C T C T C G A G C G T T C T C |
| K23 | T C G A G C G T T C T C |
| K82 | A C T C T G G A G C G T T C T C |
| K83 | A C T C T C G A G G G T T C T C |
| K84 | A C T C T C G A G C G T T C T A |
| K85 | C A T C T C G A G C G T T C T C |
| K89 | A C T C T T T C G T T C T C |
| K109 | T C G A G C G T T C T |
| K110 | T C G A G G C T T C T C |
| K123 | T C G T T C G T T C T C |
| Control ODN | |
| K121 | A C T C T T G A G T G T T C T C |

*The CpG motif is underlined in each ODN.

ODNs K3, K19 and K23 were the most effective at inducing proliferation, stimulating significant (>5-fold) proliferation by >90% of donor samples (Table 14).

TABLE 14

Percent of Donor Samples Responding to Stimulation by Individual ODN

| ODN | Proliferation | IL-6 Production | IgM Production | ALL |
|---|---|---|---|---|
| K3 | 93 (54) | 82 (50) | 59 (49) | 62 (38) |
| K19 | 92 (76) | 52 (61) | 88 (56) | 48 (42) |
| K23 | 93 (44) | 71 (45) | 55 (33) | 64 (28) |
| K82 | 88 (8) | 56 (9) | 89 (9) | 63 (8) |
| K83 | 63 (8) | 67 (9) | 78 (9) | 63 (8) |
| K84 | 67 (9) | 73 (11) | 89 (9) | 63 (8) |
| K85 | 56 (9) | 73 (11) | 89 (9) | 60 (8) |
| K89 | 57 (7) | 67 (9) | 57 (7) | 50 (6) |
| K109 | 67 (9) | 64 (11) | 71 (7) | 57 (7) |
| K110 | 81 (68) | 36 (58) | 60 (53) | 27 (41) |
| K123 | 90 (70) | 52 (54) | 65 (55) | 43 (46) |
| K121(nonCG) | 21 (68) | 11 (47) | 35 (49) | 3 (39) |

*$5 \times 10^5$ freshly isolated PBMC (N = 7-76) were stimulated with 1 µM of CpG ODN for 72 hours IL-6 and IgM levels in culture supernatants were determined by ELISA, while proliferation was measured by $^3$H-thymidine incorporation. The percent of donor samples with significantly elevated responses to each ODN (exceeding media alone by >5-fold) is shown. The number of samples tested for each condition is indicated in parentheses. The percent of subjects responding (>5-fold) in all 3 assays (ALL, N = 6-46) is provided in the final column. Not all PBMC samples were tested in all assays, and these were not included in the "ALL" analysis.

Of note, each of these ODNs contains at least two different CpG motifs (including CTCGAG and AGCGTT). By comparison, ODNs K83 and K89 (which express a single CpG motif) failed to trigger over a third of the PBMC samples to proliferate. Control ODN stimulated a response in only 20% of the donor samples and the magnitude of the response was significantly lower (p<0.05) compared to CpG ODNs (Table 14). None of the CpG ODNs studied was able to stimulate cells from every donor to proliferate.

IL-6 and IgM production were also analyzed. Greater than 80% of donor samples were stimulated to secrete IL-6 by ODN K3 (Table 14), which, as noted above, expresses multiple different CpG motifs. By comparison, ODNs expressing a single motif (even if that motif was present in multiple copies) were less active (i.e. K82, K89, K110 and K123). There was no discernable pattern for IgM secretion with respect to the length or number of CpG motifs contained in an ODN, however the phosphorothioate backbone contributes considerably to IgM induction since many individuals responded to the non-CpG ODN (Table 14). Importantly, there was some bias in the type of stimulation elicited by certain ODNs. For example, K110 was one of the strongest inducers of proliferation but was relatively weak at stimulating IgM or IL-6 secretion, whereas K3 was a potent inducer of proliferation and IL-6 production, but not IgM secretion (Table 14).

To examine the breadth of the stimulatory response elicited by individual ODN, their ability to simultaneously trigger at least a 5 fold increase in the response for three exemplary immune parameters (proliferation, IgM and IL-6 production) was examined. Whereas some ODNs were very effective at inducing one or two responses, no single ODN elicited all three types of response in greater than 64% of the donor pool (Table 14). For example, K3 stimulated 92% of the PBMC samples to proliferate and 82% to produce IL-6, but triggered only 59% of the same donors to produce IgM (Table 14). Of note, the control ODN elicited a comprehensive response in only 3% of the subjects (Table 14).

To determine whether assay variability contributed to this heterogeneity, the response of freshly isolated PBMC from the same donors was monitored on multiple occasions. An individual's pattern of reactivity to each ODN was quite reproducible, indicating that the observed heterogeneity was not due to assay variability.

Several novel insights are provided by this series of studies: 1) Although PBMC from all donors respond to at least one member of the ODN panel, no single ODN activated PBMC from all donors in all assays. 2) Different ODNs were frequently required for the induction of optimal IL-6, IgM and proliferative responses by the same subject. 3) ODNs containing multiple CpG motifs were generally more active than those containing a single motif for stimulating proliferation and IL-6 production.

Example 7

This example demonstrates that ODN mixtures are broadly immunostimulatory.

To overcome the limitations associated with the use of individual ODNs, mixtures were prepared from ODNs selected for their strong activity on PBMC from different subjects in different assays. Preliminary studies (see above) showed that mixtures that included three ODNs were optimally effective. Several such mixtures stimulated a significantly broader pool of donor PBMC in more assays than any single ODN (Table 15).

TABLE 15

Percent of Donor Samples Responding to Stimulation by K type ODN Mixtures*

| ODN Mixture | | | Proliferation | IL-6 | IgM | ALL |
|---|---|---|---|---|---|---|
| K3 | K19 | K110 | 96 (25) | 95 (19) | 91 (23) | 94 (17) |
| K19 | K23 | K123 | 100 (17) | 86 (14) | 100 (14) | 83 (12) |

TABLE 15-continued

Percent of Donor Samples Responding to Stimulation by K type ODN Mixtures*

| ODN Mixture | | | Proliferation | IL-6 | IgM | ALL |
|---|---|---|---|---|---|---|
| K3 | K110 | K123 | 94 (17) | 93 (15) | 87 (15) | 77 (13) |
| K3 | K23 | K123 | 95 (20) | 78 (18) | 89 (18) | 67 (15) |
| K3 | K19 | K123 | 95 (20) | 67 (18) | 83 (18) | 53 (15) |
| K19 | K110 | K123 | 77 (31) | 50 (20) | 82 (22) | 35 (17) |

*$5 \times 10^5$ freshly isolated PBMC (N = 12-31) were stimulated with mixtures of three ODNs (0.33 µM of each component to yield a final concentration of 1 µM for the mixture) for 72 hours. The percent of donor samples responding by proliferating or producing IL-6, IgM or all three responses (ALL, N = 12-17) was determined as described in the legend to Table 3. The number of samples tested for each condition is shown in parentheses.

The most effective mixture (composed of 0.33 µM each of K3, K19 and K110 yielding a composite ODN concentration of 1 µM) stimulated 94% of donors to proliferate and secrete IgM and IL-6. This significantly exceeded the breadth of the activity elicited by any single ODN at a concentration of 1 µM (p<0.05). Thus, this mixture of ODNs exceeded the ability of individual ODN to trigger a diverse population of donors to mount a broad range of immune responses.

To examine the magnitude of the stimulation elicited by this mixture, the response induced by K3/K19/K110 was compared to each of its components on 11 donors. In this study, individual ODNs were used at a concentration of 1 µM while each component of the mixture was used at 0.33 µm, yielding a final concentration of 1 µM. On average, the mixture stimulated a 13-fold increase in proliferation, a 6-fold increase in IL-6 production, and an 11-fold increase in IgM secretion. The response to the mixture did not differ significantly from the stimulation induced by the most active single ODN in each of these assays.

Murine studies suggest that CpG ODNs are useful as immunotherapeutic agents. However, ODNs that are highly active in mice are poorly immunostimulatory in man. Considerable effort has been invested in identifying ODNs capable of activating human cells. The described CpG ODNs vary dramatically in sequence, structure, as well as CpG number and placement. No studies thus far have specifically addressed heterogeneity in the human response to CpG ODNs. In this example, 11 highly active ODNs selected from a panel of >100 sequences were used to stimulate IgM, IL-6 and proliferative responses in PBMC from a large and diverse panel of normal donors. Results indicate that the human response to CpG ODNs is heterogeneous. No single ODN was stimulatory in all donors, and optimal Ig, cytokine and proliferative responses were commonly elicited by different ODNs, even in the same donor. A mixture was identified that induced a broader response in a greater fraction of donors than any single ODN.

Without being bound by theory, there are several potential sources for this heterogeneity. Since CpG ODNs trigger monocytes to secrete IL-6, B cells to secrete IgM, and multiple cell types to proliferate, heterogeneity between individuals may reflect differences in the relative frequency of each cell type as well as the reactivity of each cell population to specific CpG motifs. That is, if B cells respond better to K3 than K19, subjects who have higher number of B cells might show a stronger response to K3. Additional variability may arise from previous exposure to CpG DNA from environmental sources (such as pathogens or vaccines)- exposures that vary between individuals and might alter their subsequent response to specific ODNs.

Without being bound by theory, superimposed on this subject-to-subject variability may be population-based differences in CpG recognition. For example, pathogens endemic to distinct geographic locations may express different CpG motifs, and thus exert selective pressure leading to divergence in CpG recognition by inhabitants of those locations. Consistent with such a possibility is the finding that CpG recognition by rodents and primates has diverged over evolutionary periods.

It should be noted that the heterogeneity in the response was not due to inter assay variation since the individual pattern of response to CpG ODNs was reproducible in subjects tested on multiple occasions with the same sequences. Care was also taken to minimize the effect of sequence independent stimulation associated with the use of phosphorothioate ODNs. Specifically, ODNs were studied at the low fixed concentration of 1 µM, and responses were considered positive only if they exceeded background by >5-fold (since control ODN rarely induced such strong non-specific stimulation, FIG. 1).

A critical finding from the current work is that a mixture of ODNs is more broadly active than any single ODN. Each component of the optimally stimulatory mixture identified in this study expressed a different CpG motif at its 5' end—the site of greatest immunostimulatory activity. Apparently, without being bound by theory, PBMC recognize and respond to motifs that are stimulatory in that individual without interference by sequences that are less active.

Example 8

The response to D ODN was also investigated. Briefly, mononuclear cells were isolated from normal donors by density gradient centrifugation over Ficoll-Hypaque. Cells were cultured for 72 hours in RPMI supplemented with 10% heat inactivated FCS, 100 U/ml penicillin, 100 µg/ml streptomycin, and 2 mM L-glutamine. ODNs were synthesized at the CBER Core Facility.

| | | |
|---|---|---|
| D19* | GGtgcatcgatgcagGGGGG | (SEQ ID NO: 32) |
| D29* | GGtgcaccggtgcagGGGGG | (SEQ ID NO: 42) |
| D113* | GGtgcatgcatacagGGGGG | (SEQ ID NO: 106) |
| D35* | GGtgcatcgatgcagggGG | (SEQ ID NO: 32) |
| D28* | GGtgcgtcgatgcagGGGGG | (SEQ ID NO: 40) |
| D103* | GGtcaccgtggcagGGGGG | (SEQ ID NO: 118) |
| D106* | GGtgtgtcgatgcagGGGGG | (SEQ ID NO: 102) |
| D122* | GGtgcattgatgcagGGGGG | (SEQ ID NO: 107) |
| AA3M* | GGgcatgcatgGGGGG | (SEQ ID NO: 119) |

*bases shown in capital letters are phosphorothioate while those in lower case are phosphodiester All ODN contained less than 0.1 EU/mg of endotoxin as measured by the Limulus amoebocyte lysate. $5 \times 10^5$ PBMC were stimulated in vitro for 72 hours with 1 µM ODN. Expression of Interferon gamma was then assessed using standard methods. For example, culture supernatants were detected by ELISA (For example, see *Gold Book of Immunological Assays*, of Harlow and Lane, "Antibodies, a Laboratory Mannual," Cold Spring Harbor Laboratory, New York, 1988). ELISA results were quantitated using standard curves generated using recombinant IFN-γ. The limit of detection of the assays was 5-20 pg/ml. In those cases where interferon production was below assay sensitivity, the lower limit of detection was used to calculate the stimulation index. All assays were performed in triplicate. ODNs were considered stimulatory if the response they induced exceeded that of unstimulated PBMC from that subject by >5-fold. This minimized the effect of sequence-independent background stimulation associated with the use of phosphorothioate ODN.

TABLE 16

IFN-γ response of normal donors to a panel of D ODN

| ODN | % responders | N |
|---|---|---|
| D19 | 93 | 42 |
| D29 | 91 | 23 |
| D113 | 87 | 23 |
| D35 | 82 | 17 |
| D28 | 79 | 19 |
| D103 | 58 | 12 |
| D106 | 57 | 28 |
| D122 | 10 | 31 |
| AA3M | 11 | 19 |

None of the D type ODN including a CpG motif stimulated all of the subjects. However, some of the D type ODN stimulated a plurality of subjects.

Combinations of D type ODN were then assessed. The results are shown in Table 17.

TABLE 17

Effect of using mixtures of D ODN on IFN-γ response

| D-Mixture | | | % responders | N = |
|---|---|---|---|---|
| D19 | D28 | D113 | 100 | 5 |
| D35 | D28 | D113 | 100 | 5 |
| D19 | D106 | D113 | 89 | 19 |
| D35 | D28 | D29 | 80 | 5 |
| D35 | D106 | D113 | 40 | 5 |
| D19 | D28 | D29 | 40 | 5 |

Thus, a composition including D19, D28, and D113, a composition including D35, D28, and D113, a composition including D19, D106, and D113, and a composition including D35, D28, and D29 induced an immune response in 80% or more of the subjects in the population.

It will be apparent that the precise details of the methods or compositions described may be varied or modified without departing from the spirit of the described invention. We claim all such modifications and variations that fall within the scope and spirit of the claims below.

We claim:

1. An oligodeoxynucleotide composition comprising a first oligodeoxynucleotide of 20 to 50 nucleotides in length, wherein the first oligodeoxynucleotide comprises SEQ ID NO: 42;
a second oligodeoxynucleotide of 20 to 50 nucleotides in length, wherein the second oligodeoxynucleotide comprises the nucleic acid sequence set forth as SEQ ID NO: 32; and
a third oligodeoxynucleotide of 20 to 50 nucleotides in length, wherein the third oligodeoxynucleotide comprises the nucleic acid sequence set forth as SEQ ID NO: 40;
wherein the first oligodeoxynucleotide, the second oligodeoxynucleotide and the third oligodeoxynucleotide each comprise an unmethylated CpG motif, and wherein the first oligodeoxynucleotide, the second oligodeoxynucleotide and the third oligodeoxynucleotide are modified to prevent degradation, and wherein the composition induces an immune response in at least 80 percent of individuals in a population.

2. The oligodeoxynucleotide composition of claim 1, wherein the first oligodeoxynucleotide comprises multiple CpG motifs.

3. The oligodeoxynucleotide composition of claim 1, wherein the first and the second oligodeoxynucleotides each comprise multiple CpG motifs.

4. The oligodeoxynucleotide composition of claim 1, wherein the first oligodeoxynucleotide, the second oligodeoxynucleotide and/or the third oligodeoxynucleotide comprise phosphodiester bases.

5. The oligodeoxynucleotide composition of claim 1, wherein the first oligodeoxynucleotide, the second oligodeoxynucleotide and/or the third oligodeoxynucleotide comprise one or more phosphorothioate bases.

6. The oligodeoxynucleotide composition of claim 1, wherein the first oligodeoxynucleotide, the second oligodeoxynucleotide and/or the third oligodeoxynucleotide comprise a targeting moiety.

7. The oligodeoxynucleotide composition of claim 6, wherein the targeting moiety is selected from the group consisting of a cholesterol, a virosome, a liposome, a lipid, and a target cell specific binding agent.

8. A pharmaceutical composition comprising a therapeutically effective amount of the oligodeoxynucleotide composition of claim 1 in a pharmaceutically acceptable carrier.

9. A method for stimulating an immune response in a subject, comprising administering to the subject a therapeutically effective amount of the oligodeoxynucleotide composition of claim 1, thereby stimulating the immune response, wherein the immune response is substantially stimulated as compared to administration of the first oligodeoxynucleotide.

10. The method of claim 9, wherein the immune response comprises the production of interferon gamma.

11. A method for stimulating an immune response in a subject, comprising administering to the subject a therapeutically effective amount of the oligodeoxynucleotide composition of claim 6, thereby stimulating the immune response.

12. The method of claim 11, wherein the immune response comprises the production of interferon gamma.

13. The oligodeoxynucleotide composition of claim 1, wherein the third oligodeoxynucleotide comprises phosphodiester bases.

14. The oligodeoxynucleotide composition of claim 1, wherein the third oligodeoxynucleotide comprises one or more phosphorothioate bases.

15. The oligodeoxynucleotide composition of claim 1, wherein the third oligodeoxynucleotide comprises a targeting moiety.

16. The oligodeoxynucleotide composition of claim 15, wherein the targeting moiety is selected from the group consisting of a cholesterol, a virosome, a liposome, a lipid, and a target cell specific binding agent.

17. A pharmaceutical composition comprising a therapeutically effective amount of the oligodeoxynucleotide composition of claim 6 in a pharmaceutically acceptable carrier.

18. The pharmaceutical composition of claim 1, wherein the first oligodeoxynucleotide consists of the nucleic acid sequence set forth as SEQ ID NO: 42 and the second oligodeoxynucleotide consists of the nucleic acid sequence set forth as SEQ ID NO: 32.

19. The pharmaceutical composition of claim 18, wherein the third oligodeoxynucleotide consists of the nucleic acid sequence set forth as SEQ ID NO: 40.

* * * * *

```
SEQUENCE LISTING

<160> NUMBER OF SEQ ID NOS: 112

<210> SEQ ID NO 1
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 1
tcgagcgttc tc                                                            12

<210> SEQ ID NO 2
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 2
atcgactctc gagcgttct                                                     19

<210> SEQ ID NO 3
<211> LENGTH: 24
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 3
tcgtcgtttt gtcgttttgc tgtt                                               24
```

```
<210> SEQ ID NO 4
<211> LENGTH: 14
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 4
tctcgagcgt tctc                                                       14

<210> SEQ ID NO 5
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 5
tcgactctcg agcgttctc                                                  19

<210> SEQ ID NO 6
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 6
atcgactagc gttcgttctc                                                 20

<210> SEQ ID NO 7
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 7
actctcgagc gttctc                                                     16

<210> SEQ ID NO 8
<211> LENGTH: 15
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 8
ctctcgagcg ttctc                                                      15

<210> SEQ ID NO 9
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 9
gtcgacgttg ac                                                         12

<210> SEQ ID NO 10
<211> LENGTH: 12
```

```
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 10
gtcggcgttg ac                                                          12

<210> SEQ ID NO 11
<211> LENGTH: 18
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 11
cgactctcga gcgttctc                                                    18

<210> SEQ ID NO 12
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 12
gtcgacgctg ac                                                          12

<210> SEQ ID NO 13
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 13
gtcagcgttg ac                                                          12

<210> SEQ ID NO 14
<211> LENGTH: 17
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 14
gactctcgag cgttctc                                                     17

<210> SEQ ID NO 15
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 15
gtcgtcgatg ac                                                          12

<210> SEQ ID NO 16
<211> LENGTH: 20
<212> TYPE: DNA
<213> ORGANISM: Artifical Sequence
```

```
<220> FEATURE:
<223> OTHER INFORMATION: Description of Artificial Sequence: Synthetic
      DNA

<400> SEQUENCE: 16
atgcactctc gagcgttctc                                                20

<210> SEQ ID NO 17
<211> LENGTH: 13
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 17
ctcgagcgtt ctc                                                       13

<210> SEQ ID NO 18
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 18
tgcagcgttc tc                                                        12

<210> SEQ ID NO 19
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 19
tttggcgttt tt                                                        12

<210> SEQ ID NO 20
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 20
atcgactctc gagcgttctc                                                20

<210> SEQ ID NO 21
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 21
agcgtttctc gatcgacctc                                                20

<210> SEQ ID NO 22
<211> LENGTH: 19
<212> TYPE: DNA
<213> ORGANISM: Artifical Sequence
<220> FEATURE:
<223> OTHER INFORMATION: Description of Artificial Sequence: Synthetic
```

DNA

<400> SEQUENCE: 22
ggtgcaccga tgcaggggg                                                        19

<210> SEQ ID NO 23
<211> LENGTH: 14
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 23
gtcgtcgacg acgg                                                             14

<210> SEQ ID NO 24
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 24
gggggcgttg gg                                                               12

<210> SEQ ID NO 25
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 25
atgcactctg cagcgttctc                                                       20

<210> SEQ ID NO 26
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 26
atcgactctc gaggcttctc                                                       20

<210> SEQ ID NO 27
<211> LENGTH: 17
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 27
ggtgcatcga tgcaggg                                                          17

<210> SEQ ID NO 28
<211> LENGTH: 25
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 28
gggtcgtcgt tttgtcgttt cgttg                                    25

<210> SEQ ID NO 29
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 29
aaaggcgtta aa                                                  12

<210> SEQ ID NO 30
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 30
cccggcgttc cc                                                  12

<210> SEQ ID NO 31
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 31
gtcatcgatg ca                                                  12

<210> SEQ ID NO 32
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 32
ggtgcatcga tgcagggggg                                          20

<210> SEQ ID NO 33
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 33
ggggtcatcg atgaaaaaaa                                          20

<210> SEQ ID NO 34
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 34

-continued ggtgcatcga tgcagggggg                                              20

<210> SEQ ID NO 35
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 35
aaggtcaacg ttgaaaaaaa                                              20

<210> SEQ ID NO 36
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 36
aaggtcatcg atgggggggg                                              20

<210> SEQ ID NO 37
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 37
ggtgcatcga tgcaggggg                                               20

<210> SEQ ID NO 38
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 38
ggtgcatcga tgcagggggg                                              20

<210> SEQ ID NO 39
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 39
ggtgcgtcga cgcagggggg                                              20

<210> SEQ ID NO 40
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 40
ggtgcgtcga tgcagggggg                                              20

```
<210> SEQ ID NO 41
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 41
ggtgcgtcga cgcagggggg                                              20

<210> SEQ ID NO 42
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 42
ggtgcaccgg tgcagggggg                                              20

<210> SEQ ID NO 43
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 43
ggtgcatcga tgcagggggg                                              20

<210> SEQ ID NO 44
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 44
gtcaacgtcg ac                                                      12

<210> SEQ ID NO 45
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 45
gtcggcgtcg ac                                                      12

<210> SEQ ID NO 46
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 46
ggggtcaacg ttgaggggg                                               19

<210> SEQ ID NO 47
```

```
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 47
gtcggcgctg ac                                                            12

<210> SEQ ID NO 48
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 48
atgcactctc gaggcttctc                                                    20

<210> SEQ ID NO 49
<211> LENGTH: 17
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 49
aatgcatcga tgcaaaa                                                       17

<210> SEQ ID NO 50
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 50
gtcagcgtcg ac                                                            12

<210> SEQ ID NO 51
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 51
gtcaacgttg ac                                                            12

<210> SEQ ID NO 52
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 52
tgcatcgatg ca                                                            12

<210> SEQ ID NO 53
<211> LENGTH: 19
<212> TYPE: DNA
```

```
<213> ORGANISM: Artifical Sequence
<220> FEATURE:
<223> OTHER INFORMATION: Description of Artificial Sequence: Synthetic
      DNA

<400> SEQUENCE: 53
ggtgcatcga tgcaggggg                                               19

<210> SEQ ID NO 54
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 54
gtcgacgtcg ac                                                      12

<210> SEQ ID NO 55
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 55
gtcgacgccg ac                                                      12

<210> SEQ ID NO 56
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 56
cccaacgttc cc                                                      12

<210> SEQ ID NO 57
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 57
gtcaacgctg ac                                                      12

<210> SEQ ID NO 58
<211> LENGTH: 10
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 58
gagcgttctc                                                         10

<210> SEQ ID NO 59
<211> LENGTH: 12
<212> TYPE: DNA
<213> ORGANISM: Artifical Sequence
<220> FEATURE:
```

<223> OTHER INFORMATION: Description of Artificial Sequence: Synthetic
      DNA

<400> SEQUENCE: 59
gggaacgttg gg                                                          12

<210> SEQ ID NO 60
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 60
gtcagcgctg ac                                                          12

<210> SEQ ID NO 61
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 61
gggggaacgt tcgggg                                                      16

<210> SEQ ID NO 62
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 62
gtcggcgccg ac                                                          12

<210> SEQ ID NO 63
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 63
ggggtaacgt tagggg                                                      16

<210> SEQ ID NO 64
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 64
gtcaacgccg ac                                                          12

<210> SEQ ID NO 65
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 65
tgcctcgagg ca                                                              12

<210> SEQ ID NO 66
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 66
tttaacgttt tt                                                              12

<210> SEQ ID NO 67
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 67
aaaaacgtta aa                                                              12

<210> SEQ ID NO 68
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 68
gggggaagct tcgggg                                                          16

<210> SEQ ID NO 69
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 69
gtcagcgccg ac                                                              12

<210> SEQ ID NO 70
<211> LENGTH: 11
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 70
cgagcgttct c                                                               11

<210> SEQ ID NO 71
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 71

```
ggtgcatcga tgcagg                                                       16

<210> SEQ ID NO 72
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 72
ggtgcatcga tgcagggggg                                                   20

<210> SEQ ID NO 73
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 73
ggtgcatcga tgcaggggg                                                    19

<210> SEQ ID NO 74
<211> LENGTH: 13
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 74
ggcgtcgacg ggg                                                          13

<210> SEQ ID NO 75
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 75
ggtgcgtcgt tgcagggggg                                                   19

<210> SEQ ID NO 76
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 76
ggtgcgccga tgcaggggg                                                    19

<210> SEQ ID NO 77
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 77
gggggatcga tcgggg                                                       16
```

```
<210> SEQ ID NO 78
<211> LENGTH: 13
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 78
ggggtcgaca ggg                                                          13

<210> SEQ ID NO 79
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 79
ggtgcgtcgg tgcaggggg                                                    19

<210> SEQ ID NO 80
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 80
gggggatgca tcgggg                                                       16

<210> SEQ ID NO 81
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 81
ggtgcgtcga tgcagggggg                                                   20

<210> SEQ ID NO 82
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 82
ggtgcgtcga tgcagggggg                                                   20

<210> SEQ ID NO 83
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 83
ggtgcgtcga tgcaggggg                                                    19
```

```
<210> SEQ ID NO 84
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 84
ggtgcctcga ggcagggggg                                              19

<210> SEQ ID NO 85
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 85
gggggctcga gagggg                                                  16

<210> SEQ ID NO 86
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 86
ggggtatcga tagggg                                                  16

<210> SEQ ID NO 87
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 87
ggtgcatcga tgcgagaga                                               19

<210> SEQ ID NO 88
<211> LENGTH: 19
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 88
ggtgcatcga cgcaggggg                                               19

<210> SEQ ID NO 89
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 89
ggggtcaacg ttgaggggggg                                             20

<210> SEQ ID NO 90
<211> LENGTH: 20
```

```
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 90
ggtgcatgca tgcagggggg                                              20

<210> SEQ ID NO 91
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 91
ggggtcaagc ttgagggggg                                              20

<210> SEQ ID NO 92
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 92
ggggtaagct tagggg                                                  16

<210> SEQ ID NO 93
<211> LENGTH: 17
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 93
ggtgcatgca tgcaggg                                                 17

<210> SEQ ID NO 94
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 94
ggtgcataaa tgcagggggg                                              20

<210> SEQ ID NO 95
<211> LENGTH: 17
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 95
aatgcatgca tgcaaaa                                                 17

<210> SEQ ID NO 96
<211> LENGTH: 20
<212> TYPE: DNA
<213> ORGANISM: Artifical Sequence
```

```
<220> FEATURE:
<223> OTHER INFORMATION: Description of Artificial Sequence: Synthetic
      DNA

<400> SEQUENCE: 96
ggtgcatgca tgcagggggg                                                20

<210> SEQ ID NO 97
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 97
atcgactctg caggcttctc                                                20

<210> SEQ ID NO 98
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 98
tcgaggcttc tc                                                        12

<210> SEQ ID NO 99
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 99
atgcactctg caggcttctc                                                20

<210> SEQ ID NO 100
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 100
ggtgcatcga cgcagggggg                                                20

<210> SEQ ID NO 101
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 101
ggtgcaccga tgcagggggg                                                20

<210> SEQ ID NO 102
<211> LENGTH: 20
<212> TYPE: DNA
<213> ORGANISM: Artifical Sequence
<220> FEATURE:
<223> OTHER INFORMATION: Description of Artificial Sequence: Synthetic
```

DNA

<400> SEQUENCE: 102
ggtgtgtcga tgcagggggg                                           20

<210> SEQ ID NO 103
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 103
ggtgcaccgt ggcagggggg                                           20

<210> SEQ ID NO 104
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 104
ggtgcatcgt tgcagggggg                                           20

<210> SEQ ID NO 105
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 105
tcgtttgttc tc                                                   12

<210> SEQ ID NO 106
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 106
ggtgcatcga tacagggggg                                           20

<210> SEQ ID NO 107
<211> LENGTH: 20
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 107
ggtgcattga tgcagggggg                                           20

<210> SEQ ID NO 108
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA -continued

```
<400> SEQUENCE: 108
tcgttcgttc tc                                                          12

<210> SEQ ID NO 109
<211> LENGTH: 14
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 109
actctttcgt tctc                                                        14

<210> SEQ ID NO 110
<211> LENGTH: 14
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 110
actctttcga tctc                                                        14

<210> SEQ ID NO 111
<211> LENGTH: 12
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 111
tgcaggcttc tc                                                          12

<210> SEQ ID NO 112
<211> LENGTH: 16
<212> TYPE: DNA
<213> ORGANISM: Artifical Sequence
<220> FEATURE:
<223> OTHER INFORMATION: Description of Artificial Sequence: Synthetic
      DNA

<400> SEQUENCE: 112
actcttgagt gttctc                                                      16
```